US009924647B2

(12) United States Patent
Richael et al.

(10) Patent No.: US 9,924,647 B2
(45) Date of Patent: *Mar. 27, 2018

(54) POTATO CULTIVAR X17

(71) Applicant: J.R. Simplot Company, Boise, ID (US)

(72) Inventors: Craig Richael, Meridian, ID (US); Hua Yan, Boise, ID (US); Jolyn Rasmussen, Meridian, ID (US); Hui Duan, Boise, ID (US); Nicolas Champouret, Boise, ID (US); Alexi Balmuth, Boise, ID (US); Jingsong Ye, Boise, ID (US)

(73) Assignee: J.R. Simplot Company, Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/288,332

(22) Filed: Oct. 7, 2016

(65) Prior Publication Data
US 2017/0099793 A1    Apr. 13, 2017

Related U.S. Application Data

(60) Provisional application No. 62/256,942, filed on Nov. 18, 2015, provisional application No. 62/239,060, filed on Oct. 8, 2015.

(51) Int. Cl.
| *A01H 5/04* | (2018.01) |
| *A01H 1/02* | (2006.01) |
| *C12N 15/82* | (2006.01) |
| *A23L 19/18* | (2016.01) |
| *A23L 19/12* | (2016.01) |
| *A23L 19/15* | (2016.01) |

(52) U.S. Cl.
CPC ............... *A01H 5/04* (2013.01); *A01H 1/02* (2013.01); *A23L 19/14* (2016.08); *A23L 19/15* (2016.08); *A23L 19/18* (2016.08); *C12N 15/8245* (2013.01); *C12N 15/8247* (2013.01); *C12N 15/8274* (2013.01); *C12N 15/8275* (2013.01); *C12N 15/8277* (2013.01); *C12N 15/8278* (2013.01); *C12N 15/8281* (2013.01); *C12N 15/8282* (2013.01); *C12N 15/8283* (2013.01); *C12N 15/8286* (2013.01); *C12N 15/8289* (2013.01); *A23V 2002/00* (2013.01)

(58) Field of Classification Search
None
See application file for complete search history.

(56) References Cited

U.S. PATENT DOCUMENTS

| 5,510,253 | A | 4/1996 | Mitsky et al. |
| 6,160,204 | A | 12/2000 | Steffens |
| 6,855,669 | B2 | 2/2005 | Knowles et al. |
| 7,122,719 | B2 | 10/2006 | Hakimi |
| 7,250,554 | B2 | 7/2007 | Rommens et al. |
| 7,534,934 | B2 | 5/2009 | Rommens et al. |
| 7,619,138 | B2 | 11/2009 | Rommens et al. |
| 7,713,735 | B2 | 5/2010 | Rommens et al. |
| 7,880,057 | B2 | 2/2011 | Rommens et al. |
| 7,947,868 | B2 | 5/2011 | Rommens et al. |
| 8,143,477 | B2 | 3/2012 | Rommens |
| 8,158,414 | B2 | 4/2012 | Rommens et al. |
| 8,193,412 | B2 | 6/2012 | Rommens et al. |
| 8,252,974 | B2 | 8/2012 | Rommens |
| 8,273,949 | B2 | 9/2012 | Rommens et al. |
| 8,502,027 | B2 | 8/2013 | Rommens |
| 8,674,177 | B2 | 3/2014 | Rommens et al. |
| 8,710,311 | B1 * | 4/2014 | Clark ................. C12N 15/8279 435/419 |
| 8,754,303 | B1 | 6/2014 | Clark et al. |
| 8,889,963 | B1 | 11/2014 | Clark et al. |

(Continued)

FOREIGN PATENT DOCUMENTS

| JP | 2009-508526 A | 3/2009 |
| WO | WO 1994/003607 A1 | 2/1994 |

(Continued)

OTHER PUBLICATIONS

Adang, Michael J., et al., "The reconstruction and expression of a Bacillus thuringiensis cryIIIA gene in protoplasts and potato plants." Plant Molecular Biology (1993); 21: 1131-1145.

(Continued)

*Primary Examiner* — Cathy Kingdon Worley
(74) *Attorney, Agent, or Firm* — Cooley LLP

(57) ABSTRACT

A potato cultivar designated X17 is disclosed. The invention relates to the tubers of potato cultivar X17, to the seeds of potato cultivar X17, to the plants of potato cultivar X17, to the plant parts of potato cultivar X17, to food products produced from potato cultivar X17, and to methods for producing a potato plant produced by crossing potato cultivar X17 with itself or with another potato variety. The invention also relates to methods for producing a potato plant containing in its genetic material one or more transgenes and to the transgenic potato plants and plant parts produced by those methods. This invention also relates to potato cultivars or breeding cultivars and plant parts derived from potato variety X17, to methods for producing other potato cultivars, lines or plant parts derived from potato cultivar X17 and to the potato plants, varieties, and their parts derived from use of those methods. The invention further relates to hybrid potato tubers, seeds, plants and plant parts produced by crossing potato cultivar X17 with another potato cultivar.

29 Claims, 7 Drawing Sheets

(56) References Cited

U.S. PATENT DOCUMENTS

| | | | |
|---|---|---|---|
| 8,889,964 B1* | 11/2014 | Clark | A23L 1/216 435/419 |
| 9,328,352 B2 | 5/2016 | Richael et al. | |
| 9,873,885 B2 | 1/2018 | Richael et al. | |
| 2009/0220670 A1 | 9/2009 | Rommens et al. | |
| 2010/0199386 A1 | 8/2010 | Bhaskar et al. | |
| 2011/0099656 A1 | 4/2011 | Rockey et al. | |
| 2011/0107470 A1 | 5/2011 | Rommens | |
| 2011/0145943 A1 | 6/2011 | Hoopes | |
| 2011/0231949 A1 | 9/2011 | Hoopes | |
| 2012/0102589 A1 | 4/2012 | Rommens | |
| 2012/0144902 A1 | 6/2012 | Torres-ordonez et al. | |
| 2013/0074222 A1 | 3/2013 | Rommens et al. | |
| 2014/0328994 A1 | 11/2014 | Richael et al. | |
| 2016/0073600 A1 | 3/2016 | Richael et al. | |
| 2016/0073601 A1 | 3/2016 | Richael et al. | |
| 2016/0073602 A1 | 3/2016 | Richael et al. | |
| 2016/0095286 A1 | 4/2016 | Richael et al. | |
| 2016/0102371 A1 | 4/2016 | Ye et al. | |
| 2016/0330923 A1 | 11/2016 | Weeks et al. | |
| 2017/0099794 A1* | 4/2017 | Richael | A23L 19/18 |
| 2017/0150689 A1 | 6/2017 | Richael et al. | |

FOREIGN PATENT DOCUMENTS

| | | |
|---|---|---|
| WO | WO 2002/061101 A2 | 8/2002 |
| WO | WO 2003/069980 A2 | 8/2003 |
| WO | WO 2004/040999 A1 | 5/2004 |
| WO | WO 2007/035752 A2 | 3/2007 |
| WO | WO 2010/091018 A1 | 8/2010 |
| WO | WO 2014/178910 A1 | 11/2014 |
| WO | WO 2014/178913 A1 | 11/2014 |
| WO | WO 2014/178941 A1 | 11/2014 |
| WO | WO 2014/179276 A1 | 11/2014 |
| WO | WO 2015/195090 A1 | 12/2015 |
| WO | WO 2016/057874 A1 | 4/2016 |
| WO | WO 2016/183445 A1 | 11/2016 |
| WO | WO 2017/062831 A1 | 4/2017 |

OTHER PUBLICATIONS

PCT/US2016/056080, International Search Report and Written Opinion dated Dec. 19, 2016, 7 pages.

GenBank Accession HM363754, "Solanum verrucosum polyphenol oxidase 5 mRNA, 3' UTR." (2010); Downloaded Jun. 20, 2017, 1 page https://www.ncbi.nlm.nih.gov/nuccore/308743331?sat=4&satkey=45811437.

GenBank Accession AY566556, "Solanum tuberosum polyphenol oxidase mRNA, 3' UTR." (2004); Downloaded Jun. 20, 2017, 1 page https://www.ncbi.nlm.nih.gov/nuccore/AY566556.

Rommens, et al., "Crop improvement through modification of the plant's own genome." Plant Physiology (2004); 135: 421-431; Retracted Apr. 2, 2013 (Retractions, 135: 421-431, 2004 and Addenda 139: 1338-1349, 2005).

Firko, M.J. "Preliminary Extended Determination1 of Nonregulated Status for JR Simplot 1-29 Company X17 and Y9 Potato Varieties with Late Blight Resistance, Low Acrylamide Potential, Lowered Reducing Sugars, and Reduced Black Spot (Petition No. 16-064-01 p)," U.S. Department of Agriculture, Sep. 22, 2016 (Sep. 22, 2016), pp. 1-17. Retrieved from the Internet:<www.aphis.usda.gov/brs/aphisdocs/16_06401p_pdet_pprsa.pdf> on Nov. 20, 2016 (Nov. 20, 2016). entire document.

Kamrani et al. "Cisgenic inhibition of the potato cold induced phosphorylase L gene expression and decrease in sugar contents," African Journal of Biotechnology (2011); 10(50): 10076-10082.

Zhu et al. "Silencing of vacuolar invertase and asparagine synthetase genes and its impact on acrylamide formation of fried potato products," Plant Biotechnology Journal (2015); 14: 709-718.

PCT/US2016/056086, International Search Report and Written Opinion dated Dec. 9, 2016, 7 pages.

Chawla et al., "Tuber-specific silencing of asparagine synthetase-1 reduces the acrylamide-forming potential of potatoes grown in the field without affecting tuber shape and yield." Plant Biotechnol J. (2012); 10(8):913-924.

Budapest Certificate of Deposit, Budapest Treaty on the International Recognition of the Deposit of Microogranisms for the Purposes of Patent Procedure International Form, The American Type Culture Collection (ATCC), date of receipt of deposit Jun. 17, 2015, ATCC Designation—PTA-122246, V11 (Snowden Event), Viability Tested and Verified Dec. 15, 2015, 2 pages.

Chinese Patent Application No. 201380076275.7, Search Report (English translation) dated Sep. 13, 2016, 2 pages.

Cheng et al., "Effect of Different Varities of Potatoes on Acrylamide in Fresh-cut Fried Chips," Food Science (2011); 32(7): 141-144.

Coetzer et al., "Control of enzymatic browning in potato (Solanum tuberosum L.) by sense and antisense RNA from tomato polyphenol oxidase", J. Agric. Food Chem. (2001); vol. 49, pp. 652-657.

European Patent Application No. EP 13883574.9, Extended European Search Report dated Nov. 25, 2016, 10 pages.

European Patent Application No. EP 13883638.2, Extended European Search Report dated Nov. 25, 2016, 10 pages.

European Patent Application No. EP 14791173.9, Extended European Search Report dated Nov. 25, 2016, 10 pages.

Clark et al., "Petition for Determination of Nonregulated Status for InnateTM Potatoes with Low Acrylamide Potential and Reduced Black Spot Bruise: Events E12 and E24 (Russet Burbank); F10 and F37 (Ranger Russet); J3, J55, and J78 (Atlantic); G11 (G); H37and H50 (H)," J.R. Simplot Co.; pp. 1-525, Mar. 5, 2013, published on May 3, 2013, https://www.aphis.usda.gov/brs/aphisdocs/13_02201p.pdf.

Foster, Simon J., et al. "Rpi-vnt1. 1, a Tm-22 homolog from Solanum venturii, confers resistance to potato late blight." Molecular Plant-Microbe Interactions (2009); 22.5: 589-600.

Richael, et al., "Employment of cytokinin vectors for marker-free and backbone-free transformation", Methods Mol Biol (2012); 847: 3-10.

Richael, et al., "Cytokinin vectors mediate marker-free and backbone-free plant transformation", Transgenic Res. (2008); 17: 905-917.

Ritte et al., "The starch-related R1 protein is an α-glucan, water dikinase", PNAS (2002); 99: 7166-7171.

Rommens et al., "The intragenic approach as a new extension to traditional plant breeding", Trends in Plant Science (2007); 12(9): 397-403.

Rommens et al., "Low-acrylamide French fries and potato chips", Plant Biotechnology Journal (2008); 6(8): 843-853.

Rommens, C.M., "All-native DNA transformation: a new approach to plant genetic engineering", Trends in Plant Science (2004), 9(9): 457-464.

Rommens, C.M., "Chapter 4: Precise breeding through all-native DNA transformation in Genetic Modification of Plants", Biotechnology in Agriculture and Forestry 64 (2010); F. Kempken and C. Jung (eds), Springer-Verlag, Berlin Heidelberg.

Rommens, C.M., "Intragenic crop improvement: combining the benefits of traditional breeding and genetic engineering", J. Agric. Food Chem. (2007); 55(11): 4281-4288.

Rommens, et al., "Improving potato storage and processing characteristics through all-native DNA transformation", J. Agric. Food Chem. (2006), 54(26): 9882-9887.

Rommens, et al., Intragenic vectors and marker-free transformation: Tools for a greener biotechnology, in Plant Transformation Technologies (2010); (eds C.N. Stewart, A. Touraev, V. Citovsky and T. Tzfira), Wiley-Blackwell, Oxford, UK.

Rommens, et al., "Plant-derived transfer DNAs", Plant Physiology (2005), 139: 1338-1349.

Rommens, et al., "Tastier and healthier alternatives to French fries", J Food Sci (2010); 75(4): H109-15.

Sonnewald et al. "A second L-type isozyme of potato glucan phosphorylase: cloning, antisense inhibition and expression analysis", Plant Molecular Biology (1995); 27: 567-576.

Yan, et al., "New construct approaches for efficient gene silencing in plants", Plant Physiology (2006); 141: 1508-1518.

(56) References Cited

OTHER PUBLICATIONS

Ye, et al. "Tuber-specific silencing of the acid invertase gene substantially lowers the acrylamide-forming potential of potato", J Agric Food Chem (2010); 58(23): 12162-12167.
Chinese Patent Application No. 201480024969.0, Search Report dated May 25, 2016, 3 pages.
PCT/US2013/068543, International Search Report and Written Opinion dated Mar. 11, 2014, 10 pages.
PCT/US2013/068543, International Preliminary Report on Patentability dated Nov. 3, 2015, 4 pages.
PCT/US2013/072191, International Search Report and Written Opinion dated Feb. 12, 2014, 6 pages.
PCT/US2013/072191, International Preliminary Report on Patentability dated Nov. 3, 2015, 5 pages.
PCT/US2014/018161, International Search Report and Written Opinion dated May 22, 2014, 6 pages.
PCT/US2014/018161, International Preliminary Report on Patentability dated Nov. 3, 2015, 5 pages.
PCT/US2014/035809, International Search Report and Written Opinion dated Sep. 23, 2014, 10 pages.
PCT/US2014/035809, International Preliminary Report on Patentability dated Nov. 3, 2015, 9 pages.
PCT/US2014/042631, International Search Report and Written Opinion dated Jan. 2, 2015, 14 pages.
PCT/US2014/042631, International Preliminary Report on Patentability dated Dec. 20, 2016, 10 pages.
PCT/US2016/032359, International Search Report and Written Opinion dated Aug. 18, 2016, 8 pages.
Liu, et al., "Physicochemical properties of starches during potato growth." Carbohydrate Polymers (2003); 51(2): 213-221.
PCT/US2016/032359, International Preliminary Report on Patentability dated Nov. 14, 2017, 4 pages.
Brummell et al. "Induction of vacuolar invertase inhibitor mRNA in potato tubers contributes to cold-induced sweetening resistance and includes spliced hybrid mRNA variants." J. of Exp. Botany (2011); 62(10): 3519-3534.
Zhu et al., "Functional stacking of three resistance genes against Phytophthora infestans in potato." Transgenic Research (2012); 21(1): 89-99.

* cited by examiner

1)

2) and 3)

4)

US 9,924,647 B2

POTATO CULTIVAR X17

CROSS-REFERENCE TO RELATED APPLICATIONS

The present application claims the benefit of priority to U.S. Provisional Application No. 62/239,060, filed on Oct. 8, 2015, and U.S. Provisional Application No. 62/256,942, filed on Nov. 18, 2015, the entire contents of each of which are hereby incorporated by reference in their entirety for all purposes.

FIELD

The present disclosure relates to a novel potato cultivar designated X17 and to the tubers, plants, plant parts, tissue culture, and seeds produced by that potato variety. The disclosure further relates to food products produced from potato cultivar X17, such as French fries, potato chips, dehydrated potato material, potato flakes, and potato granules.

BACKGROUND

The potato is the world's fourth most important food crop and by far the most important vegetable. Potatoes are currently grown commercially in nearly every state of the United States. Annual potato production exceeds 18 million tons in the United States and 300 million tons worldwide. The popularity of the potato derives mainly from its versatility and nutritional value. Potatoes can be used fresh, frozen or dried, or can be processed into flour, starch or alcohol. They contain complex carbohydrates and are rich in calcium, niacin and vitamin C.

The quality of potatoes in the food industry is affected by two critical factors: (1) potatoes contain large amounts of asparagine, a non-essential free amino acid that is rapidly oxidized to form acrylamide, a carcinogenic product, upon frying or baking; and (2) potatoes are highly susceptible to enzymatic browning and discoloration, an undesirable event which happens when polyphenol oxidase leaks out from the damaged plastids of bruised potatoes. In the cytoplasm, the enzyme oxidizes phenols, which then rapidly polymerize to produce dark pigments. Tubers contain large amounts of phosphorylated starch, some of which is degraded during storage to produce glucose and fructose. These reducing sugars react with amino acids to form Maillard products including acrylamide when heated at temperatures above 120° C. Two enzymes involved in starch phosphorylation are water dikinase R1 and phosphorylase-L (R1 and PhL). Browning is also triggered non-enzymatically as a consequence of the partial degradation of starch into glucose and fructose.

Many potato cultivars are susceptible to late blight, a devastating disease caused by the fungus-like oomycete pathogen *Phytophthora infestans*. Late blight of potato is identified by black/brown lesions on leaves and stems that may expand rapidly and become necrotic. Severe late blight epidemics occur when *P. infestans* grows and reproduces rapidly on the host crop.

Thus, there is a need to develop potato varieties with reduced levels of toxic compounds and increased resistance to disease, but without the use of unknown or foreign nucleic acids. The present disclosure satisfies this need.

The foregoing examples of the related art and limitations related therewith are intended to be illustrative and not exclusive. Other limitations of the related art will become apparent to those of skill in the art upon a reading of the specification.

SUMMARY OF THE DISCLOSURE

There is thus a need in the art for potato plant varieties that produce tubers with low acrylamide content, increased black spot bruise tolerance, lowered reducing sugars, and increased resistance to late blight.

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

To this end, the present invention provides novel potato variety X17 transformed with nucleic acid sequences that are native to the potato plant genome and does not contain foreign DNA, *Agrobacterium* DNA, viral markers or vector backbone sequences. Rather, the DNA inserted into the genome of the potato variety X17 is a non-coding polynucleotide native to potato or native to wild potato, a potato sexually-compatible plant, that silences genes involved in the expression of black spot bruises, asparagine accumulation and senescence sweetening.

Thus, in one embodiment, the present invention provides a plant vector, referred to as pSIM1278, that comprises a first silencing cassette containing two copies of a DNA segment comprising, in anti-sense orientation, a fragment of the asparagine synthetase-1 gene (fAsn1) and the 3'-untranslated sequence of the polyphenol oxidase-5 gene; and a second silencing cassette containing two copies of a DNA segment comprising, in anti-sense orientation, a fragment of the potato phosphorylase-L (pPhL) gene and a fragment of the potato R1 gene. The pSIM1278 vector comprises a 9,512 bp backbone region that supports maintenance of the plant DNA prior to plant transformation and is not transferred into plant cells upon transformation of the plant cells, and a 10,148 bp DNA insert region comprising native DNA that is stably integrated into the genome of the plant cells upon transformation.

In another embodiment, the present invention provides a second plant vector, referred to as pSIM1678, which comprises the Rpi-vnt1 expression cassette and a silencing cassette for the plant vacuolar invertase gene, VInv. The Rpi-vnt1 gene cassette consists of the VNT1 protein coding region regulated by its native promoter and terminator sequences to confer broad resistance to late blight, whereas the silencing cassette consists of an inverted repeat of sequence from the potato VInv gene flanked by opposing plant promoters, pGbss and pAgp. The pSIM1678 vector comprises a 9,512 bp backbone region that supports maintenance of the plant DNA prior to plant transformation and is not transferred into plant cells upon transformation of the plant cells, and a 9,090 bp DNA insert region comprising native DNA that is stably integrated into the genome of the plant cells upon transformation.

In a different embodiment, the invention provides a plant cell transformed with one or both of the plant vectors of the invention. In a further embodiment, the invention provides a potato plant variety comprising one or more cells transformed with the vectors of the invention. In one aspect of the invention, the potato plant variety expresses at least one of the two silencing cassettes of the vector pSIM1278 and expresses the silencing cassette of the vector pSIM1678, and expression of the silencing cassettes results in the down-regulation of the asparagine synthetase-1 gene, the polyphenol oxidase-5 gene and the vacuolar invertase gene in the tubers of the plant. In a preferred aspect of the invention, the tubers of the potato plant variety expressing at least one silencing cassette display two or more desirable traits that are not present in the tubers of untransformed plants of the same variety. In the most preferred aspect of the invention, the two or more desirable traits are selected from the group consisting of low asparagine accumulation, reduced blackspot bruising, reduced heat-induced acrylamide formation and reduced accumulation of reducing sugars during storage.

In a different aspect of the invention, the potato plant variety expresses both silencing cassettes of the plant DNA vector pSIM1278, and expresses the silencing cassette of the vector pSIM1678, and expression of the silencing cassettes results in the down-regulation of the asparagine synthetase-1 gene, the polyphenol oxidase-5 gene, the phosphorylase-L gene, the dikinase R1 gene and the vacuolar invertase gene in the tubers of the potato plant variety. In a preferred aspect of the invention, the tubers of the potato plant variety expressing two silencing cassettes of the plant DNA vector pSIM1278 and expressing the silencing cassette of the vector pSIM1678 display two or more desirable traits that are not present in the tubers of untransformed plants of the same variety. In a preferred embodiment, the two or more desirable traits are selected from the group consisting of low asparagine accumulation, reduced black-spot bruising, reduced accumulation of reducing sugars during storage and reduced heat-induced acrylamide formation. In one aspect of the invention, the potato plant variety expressing the two silencing cassettes of the plant DNA vector pSIM1278 and the silencing cassette of the plant DNA vector pSIM1678 is the Ranger Russet X17 variety.

In another aspect of the invention, the potato plant variety X17 of the present invention expresses the late blight resistance gene (Rpi-vnt1) of the plant DNA vector pSIM1678. In a further aspect of the present invention, the potato plant variety X17 of the present invention has increased resistance to late blight infection.

Thus, according to the invention, there is provided a new potato cultivar of the genus and species *Solanum tuberosum* L. designated X17. This invention thus relates to potato cultivar X17, to the tubers of potato cultivar X17, to the plants of potato cultivar X17, to the seeds of potato cultivar X17, to the food products produced from potato cultivar X17, and to methods for producing a potato plant produced by selfing potato cultivar X17 or by crossing potato cultivar X17 with another potato cultivar, and the creation of variants by mutagenesis or transformation of potato cultivar X17.

Thus, any such methods using the cultivar X17 are embodiments of this invention: selfing, backcrosses, hybrid production, crosses to populations, and the like. All plants produced using potato cultivar X17 as at least one parent are within the scope of this invention. Advantageously, the potato cultivar could be used in crosses with other, different, potato plants to produce first generation ($F_1$) potato hybrid tubers, seeds and plants with superior characteristics.

In another embodiment, the present invention provides for single or multiple gene converted plants of potato cultivar X17. In one embodiment, the transferred gene(s) may be a dominant or recessive allele(s). In some embodiments, the transferred gene(s) will confer such traits as herbicide resistance, insect resistance, resistance for bacterial, fungal, or viral disease, male fertility, male sterility, enhanced nutritional quality, uniformity, and increase in concentration of starch and other carbohydrates, decrease in tendency to bruise and decrease in the rate of conversion of starch to sugars. The gene(s) may be a naturally occurring potato gene or a transgene introduced through genetic engineering techniques, backcrossing or mutation.

In another embodiment, the present invention provides regenerable cells for use in tissue culture of potato cultivar X17. In one embodiment, the tissue culture will be capable of regenerating plants having all the physiological and morphological characteristics of the foregoing potato plant, and of regenerating plants having substantially the same genotype as the foregoing potato plant. In some embodiments, the regenerable cells in such tissue cultures will be embryos, protoplasts, meristematic cells, callus, pollen, leaves, anthers, pistils, cotyledons, hypocotyl, roots, root tips, flowers, seeds, petioles, tubers, eyes or stems. Still further, the present invention provides potato plants regenerated from tissue cultures of the invention.

In a further embodiment, the invention provides a food product made from a tuber of potato plant variety Ranger Russet X17. Preferably, the food product is a heat-treated product. Even more preferably, the food product is a fresh whole potato, French fry, potato chip, dehydrated potato material, potato flakes, or potato granules.

In addition to the exemplary aspects and embodiments described above, further aspects and embodiments will become apparent by study of the following descriptions.

DETAILED DESCRIPTION

Definitions

Figure 1:
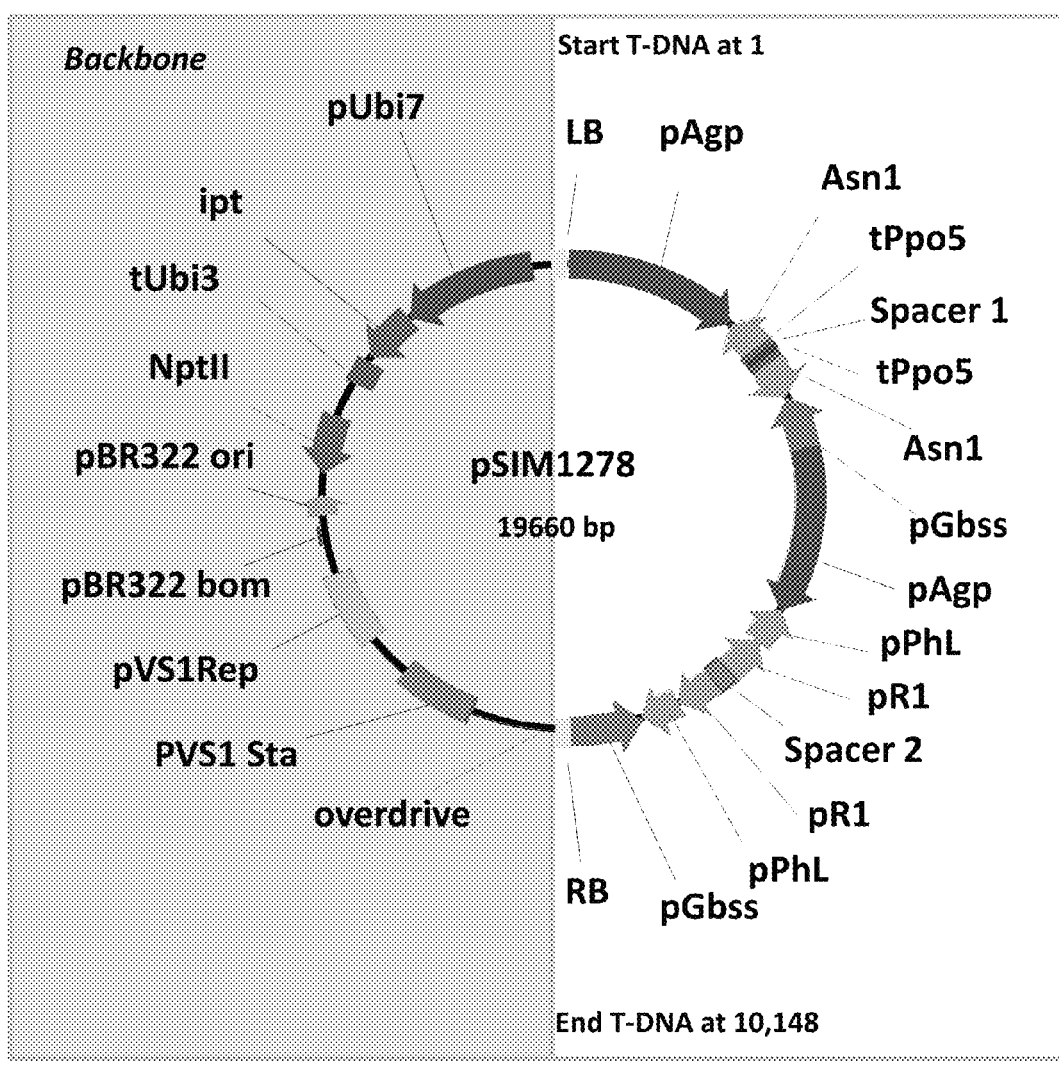
FIG. 1 depicts the pSIM1278 transformation vector. The vector backbone region, on the left, is 9,512 bp long, as it starts at position 10,149 bp and ends at position 19,660 bp. The backbone DNA consists mainly of bacterial DNA which provides support maintenance of the DNA insert prior to plant transformation. The DNA insert region (right side), including flanking Border sequences, is 10,148 bp long (from 1 bp to 10,148 bp). The DNA insert was stably integrated into the potato genome upon transformation.

In the description and tables which follow, a number of terms are used. In order to provide a clear and consistent understanding of the specification and claims, including the scope to be given such terms, the following definitions are provided.

The term "a" or "an" refers to one or more of that entity; for example, "a primer" refers to one or more primers or at least one primer. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

Allele. An allele is any of one or more alternative forms of a gene which relate to one trait or characteristic. In a diploid cell or organism, the two alleles of a given gene occupy corresponding loci on a pair of homologous chromosomes.

Amino acid sequence. As used herein, includes an oligopeptide, peptide, polypeptide, or protein and fragments thereof that are isolated from, native to, or naturally occurring in a plant, or are synthetically made but comprise the nucleic acid sequence of the endogenous counterpart.

Artificially manipulated. as used herein, "artificially manipulated" means to move, arrange, operate or control by the hands or by mechanical means or recombinant means, such as by genetic engineering techniques, a plant or plant cell, so as to produce a plant or plant cell that has a different biological, biochemical, morphological, or physiological phenotype and/or genotype in comparison to unmanipulated, naturally-occurring counterpart.

Asexual propagation. Producing progeny by generating an entire plant from leaf cuttings, stem cuttings, root cuttings, tuber eyes, stolons, single plant cells protoplasts, callus and the like, that does not involve fusion of gametes.

Backbone. Nucleic acid sequence of a binary vector that excludes the DNA insert sequence intended for transfer.

Backcrossing. Backcrossing is a process in which a breeder repeatedly crosses hybrid progeny back to one of the parents, for example, a first generation hybrid $F_1$ with one of the parental genotypes of the $F_1$ hybrid.

Bacterial Ring Rot. Bacterial ring rot is a disease caused by the bacterium *Clavibacter michiganense* ssp. Bacterial ring rot derives its name from a characteristic breakdown of the vascular ring within the tuber. This ring often appears as a creamy-yellow to light-brown, cheesy rot. On the outer surface of the potato, severely diseased tubers may show slightly sunken, dry and cracked areas. Symptoms of bacterial ring rot in the vascular tissue of infected tubers can be less obvious than described above, appearing as only a broken, sporadically appearing dark line or as a continuous, yellowish discoloration.

Black spot bruise. Black spots found in bruised tuber tissue are a result of a pigment called melanin that is produced following the injury of cells and gives tissue a brown, gray or black appearance. Melanin is formed when phenol substrates and an appropriate enzyme come in contact with each other as a result of cellular damage. The damage does not require broken cells. However, mixing of the substrate and enzyme must occur, usually when the tissue is impacted. Black spots occur primarily in the perimedullary tissue just beneath the vascular ring, but may be large enough to include a portion of the cortical tissue.

Border-like sequences. A "border-like" sequence is isolated from the selected plant species that is to be modified, or from a plant that is sexually-compatible with the plant species to be modified, and functions like the border sequences of *Agrobacterium*. That is, a border-like sequence of the present invention promotes and facilitates the integration of a polynucleotide to which it is linked. A DNA insert of the present invention preferably contains border-like sequences. A border-like sequence of a DNA insert is between 5-100 bp in length, 10-80 bp in length, 15-75 bp in length, 15-60 bp in length, 15-50 bp in length, 15-40 bp in length, 15-30 bp in length, 16-30 bp in length, 20-30 bp in length, 21-30 bp in length, 22-30 bp in length, 23-30 bp in length, 24-30 bp in length, 25-30 bp in length, or 26-30 bp in length. A DNA insert left and right border sequence are isolated from and/or native to the genome of a plant that is to be modified. A DNA insert border-like sequence is not identical in nucleotide sequence to any known *Agrobacterium*-derived T-DNA border sequence. Thus, a DNA insert border-like sequence may possess 1, 2, 3, 4, 5, 6, 7, 8, 9, 10, 11, 12, 13, 14, 15, 16, 17, 18, 19, 20, or more nucleotides that are different from a T-DNA border sequence from an *Agrobacterium* species, such as *Agrobacterium tumefaciens* or *Agrobacterium rhizogenes*. That is, a DNA insert border, or a border-like sequence of the present invention has at least 95%, at least 90%, at least 80%, at least 75%, at least 70%, at least 60% or at least 50% sequence identity with a T-DNA border sequence from an *Agrobacterium* species, such as *Agrobacterium tumefaciens* or *Agrobacterium rhizogenes*, but not 100% sequence identity. As used herein, the descriptive terms "DNA insert border" and "DNA insert border-like" are exchangeable. A border-like sequence can be isolated from a plant genome and be modified or mutated to change the efficiency by which it is capable of integrating a nucleotide sequence into another nucleotide sequence. Other polynucleotide sequences may be added to or incorporated within a border-like sequence of the present invention. Thus, a DNA insert left border or a DNA insert right border may be modified so as to possess 5'- and 3'-multiple cloning sites, or additional restriction sites. A DNA insert border sequence may be modified to increase the likelihood that backbone DNA from the accompanying vector is not integrated into the plant genome.

Consisting essentially of. A composition "consisting essentially of" certain elements is limited to the inclusion of those elements, as well as to those elements that do not materially affect the basic and novel characteristics of the inventive composition. Thus, so long as the composition does not affect the basic and novel characteristics of the instant invention, that is, does not contain foreign DNA that is not from the selected plant species or a plant that is sexually compatible with the selected plant species, then that composition may be considered a component of an inventive composition that is characterized by "consisting essentially of" language.

Cotyledon. A cotyledon is a type of seed leaf. The cotyledon contains the food storage tissues of the seed.

Degenerate primer. A "degenerate primer" is an oligo-nucleotide that contains sufficient nucleotide variations that it can accommodate base mismatches when hybridized to sequences of similar, but not exact, homology.

Dicotyledon (dicot). A flowering plant whose embryos have two seed leaves or cotyledons. Examples of dicots include, but are not limited to, tobacco, tomato, potato, sweet potato, cassava, legumes including alfalfa and soybean, carrot, strawberry, lettuce, oak, maple, walnut, rose, mint, squash, daisy, and cactus.

DNA insert. According to the present invention, the DNA insert to be inserted into the genome of a plant comprises polynucleotide sequences native to that plant or has native genetic elements to that plant. In one example, for instance, the DNA insert from pSIM1278 of the potato variety X17 of the present invention is a non-coding polynucleotide that is native to potato or wild potato, a potato sexually-compatible plant, that is stably integrated into the genome of the plant cells upon transformation and silences genes involved in the expression of black spot bruises, asparagine accumulation and senescence sweetening. The DNA insert preferably comprises two expression cassettes and is inserted into a transformation vector referred to as the pSIM1278 transformation vector. The first cassette comprises fragments of both the asparagine synthetase-1 gene (Asn1) and the polyphenol oxidase-5 gene (Ppo5), arranged as inverted repeats between the Agp promoter of the ADP glucose pyrophosphorylase gene (Agp) and the Gbss promoter of the granule-bound synthase gene (Gbss). These promoters are predominantly active in tubers. The function of the second cassette is to silence the promoters of the starch associated gene dikinase-R1 (R1) and the phosphorylase-L gene (PhL). This cassette is comprised of fragments of the promoters of the starch associated gene dikinase-R1 (R1) and the phosphorylase-L gene (PhL), operably linked to the same Agp and Gbss promoters as the first cassette. A second DNA insert comes from the transformation vector referred to as pSIM1678 that comprises the Rpi-vnt1 expression cassette and a silencing cassette for the plant vacuolar invertase gene, VInv. The Rpi-vnt1 gene cassette consists of the VNT1 protein coding region regulated by its native promoter and terminator sequences to confer broad resistance to late blight, whereas the silencing cassette consists of an inverted repeat of sequence from the potato VInv gene flanked by opposing plant promoters, pGbss and pAgp. These expression cassettes contain no foreign DNA, and consist of DNA only from either the selected plant species or from a plant that is sexually compatible with the selected plant species.

Embryo. The embryo is the immature plant contained within a mature seed.

Foreign. "Foreign," with respect to a nucleic acid, means that that nucleic acid is derived from non-plant organisms, or derived from a plant that is not the same species as the plant to be transformed or is not derived from a plant that is not interfertile with the plant to be transformed, does not belong to the species of the target plant. According to the present invention, foreign DNA or RNA represents nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not have to encode a protein product. According to the present invention, a desired intragenic plant is one that does not contain any foreign nucleic acids integrated into its genome.

Gene. As used herein, "gene" refers to the coding region and does not include nucleotide sequences that are 5'- or 3'- to that region. A functional gene is the coding region operably linked to a promoter or terminator. A gene can be introduced into a genome of a species, whether from a different species or from the same species, using transformation or various breeding methods.

Gene Converted (Conversion). Gene converted (conversion) plant refers to plants which are developed by a plant breeding technique called backcrossing wherein essentially all of the desired morphological and physiological characteristics of a variety are recovered in addition to the one or more genes transferred into the variety via the backcrossing technique, via genetic engineering or via mutation. One or more loci may also be transferred.

Genetic rearrangement. Refers to the re-association of genetic elements that can occur spontaneously in vivo as well as in vitro which introduce a new organization of genetic material. For instance, the splicing together of polynucleotides at different chromosomal loci, can occur spontaneously in vivo during both plant development and sexual recombination. Accordingly, recombination of genetic elements by non-natural genetic modification techniques in vitro is akin to recombination events that also can occur through sexual recombination in vivo.

Golden nematode. *Globodera rostochiensis*, commonly known as golden nematode, is a plant parasitic nematode affecting the roots and tubers of potato plants. Symptoms include poor plant growth, wilting, water stress and nutrient deficiencies.

Hypocotyl. A hypocotyl is the portion of an embryo or seedling between the cotyledons and the root. Therefore, it can be considered a transition zone between shoot and root.

In frame. Nucleotide triplets (codons) are translated into a nascent amino acid sequence of the desired recombinant protein in a plant cell. Specifically, the present invention contemplates a first nucleic acid linked in reading frame to a second nucleic acid, wherein the first nucleotide sequence is a gene and the second nucleotide is a promoter or similar regulatory element.

Integrate. Refers to the insertion of a nucleic acid sequence from a selected plant species, or from a plant that is from the same species as the selected plant, or from a plant that is sexually compatible with the selected plant species, into the genome of a cell of a selected plant species. "Integration" refers to the incorporation of only native genetic elements into a plant cell genome. In order to integrate a native genetic element, such as by homologous recombination, the present invention may "use" non-native DNA as a step in such a process. Thus, the present invention distinguishes between the "use of" a particular DNA molecule and the "integration" of a particular DNA molecule into a plant cell genome.

Introduction. As used herein, refers to the insertion of a nucleic acid sequence into a cell, by methods including infection, transfection, transformation or transduction.

Isolated. "Isolated" refers to any nucleic acid or compound that is physically separated from its normal, native environment. The isolated material may be maintained in a suitable solution containing, for instance, a solvent, a buffer, an ion, or other component, and may be in purified, or unpurified, form.

Late blight. A potato disease caused by the oomycete *Phytophthora infestans* and also known as 'potato blight' that can infect and destroy the leaves, stems, fruits, and tubers of potato plants.

Leader. Transcribed but not translated sequence preceding (or 5' to) a gene.

Locus. A locus confers one or more traits such as, for example, male sterility, herbicide tolerance, insect resistance, disease resistance, waxy starch, modified fatty acid metabolism, modified phytic acid metabolism, modified carbohydrate metabolism, and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Marketable Yield. Marketable yield is the weight of all tubers harvested that are between 2 and 4 inches in diameter. Marketable yield is measured in cwt (hundred weight) where cwt=100 pounds.

Monocotyledon (monocot). A flowering plant whose embryos have one cotyledon or seed leaf. Examples of monocots include, but are not limited to turf grass, maize, rice, oat, wheat, barley, sorghum, orchid, iris, lily, onion, and palm.

Native. A "native" genetic element refers to a nucleic acid that naturally exists in, orginates from, or belongs to the genome of a plant that is to be transformed. Thus, any nucleic acid, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species. In other words, a native genetic element represents all genetic material that is accessible to plant breeders for the improvement of plants through classical plant breeding. Any variants of a native nucleic acid also are considered "native" in accordance with the present invention. In this respect, a "native" nucleic acid may also be isolated from a plant or sexually compatible species thereof and modified or mutated so that the resultant variant is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in nucleotide sequence to the unmodified, native nucleic acid isolated from a plant. A native nucleic acid variant may also be less than about 60%, less than about 55%, or less than about 50% similar in nucleotide sequence. A "native" nucleic acid isolated from a plant may also encode a variant of the naturally occurring protein product transcribed and translated from that nucleic acid. Thus, a native nucleic acid may encode a protein that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in amino acid sequence to the unmodified, native protein expressed in the plant from which the nucleic acid was isolated.

Native genetic elements. "Native genetic elements" can be incorporated and integrated into a selected plant species genome according to the present invention. Native genetic elements are isolated from plants that belong to the selected plant species or from plants that are sexually compatible with the selected plant species. For instance, native DNA incorporated into cultivated potato (*Solanum tuberosum*) can be derived from any genotype of *S. tuberosum* or any genotype of a wild potato species that is sexually compatible with *S. tuberosum* (e.g., *S. demissum*).

Naturally occurring nucleic acid. Naturally occurring nucleic acid are found within the genome of a selected plant species and may be a DNA molecule or an RNA molecule. The sequence of a restriction site that is normally present in the genome of a plant species can be engineered into an exogenous DNA molecule, such as a vector or oligonucleotide, even though that restriction site was not physically isolated from that genome. Thus, the present invention permits the synthetic creation of a nucleotide sequence, such as a restriction enzyme recognition sequence, so long as that sequence is naturally occurring in the genome of the selected plant species or in a plant that is sexually compatible with the selected plant species that is to be transformed.

Operably linked. Combining two or more molecules in such a fashion that in combination they function properly in a plant cell. For instance, a promoter is operably linked to a structural gene when the promoter controls transcription of the structural gene.

Plant. As used herein, the term "plant" includes but is not limited to angiosperms and gymnosperms such as potato, tomato, tobacco, alfalfa, lettuce, carrot, strawberry, sugarbeet, cassava, sweet potato, soybean, maize, turf grass, wheat, rice, barley, sorghum, oat, oak, *eucalyptus*, walnut, and palm. Thus, a plant may be a monocot or a dicot. The word "plant," as used herein, also encompasses plant cells, seed, plant progeny, propagule whether generated sexually or asexually, and descendents of any of these, such as cuttings or seed. Plant cells include suspension cultures, callus, embryos, meristematic regions, callus tissue, leaves, roots, shoots, gametophytes, sporophytes, pollen, seeds and microspores. Plants may be at various stages of maturity and may be grown in liquid or solid culture, or in soil or suitable media in pots, greenhouses or fields. Expression of an introduced leader, trailer or gene sequences in plants may be transient or permanent. A "selected plant species" may be, but is not limited to, a species of any one of these "plants."

Plant Parts. As used herein, the term "plant parts" (or a potato plant, or a part thereof) includes but is not limited to protoplast, leaf, stem, root, root tip, anther, pistil, seed, embryo, pollen, ovule, cotyledon, hypocotyl, flower, tuber, eye, tissue, petiole, cell, meristematic cell, and the like.

Plant species. The group of plants belonging to various officially named plant species that display at least some sexual compatibility.

Plant transformation and cell culture. Broadly refers to the process by which plant cells are genetically modified and transferred to an appropriate plant culture medium for maintenance, further growth, and/or further development.

Precise breeding. Refers to the improvement of plants by stable introduction of nucleic acids, such as native genes and regulatory elements isolated from the selected plant species, or from another plant in the same species as the selected plant, or from species that are sexually compatible with the selected plant species, into individual plant cells, and subsequent regeneration of these genetically modified plant cells into whole plants. Since no unknown or foreign nucleic acid is permanently incorporated into the plant genome, the inventive technology makes use of the same genetic material that is also accessible through conventional plant breeding.

Progeny. As used herein, includes an $F_1$ potato plant produced from the cross of two potato plants where at least one plant includes potato cultivar X17 and progeny further includes, but is not limited to, subsequent $F_2$, $F_3$, $F_4$, $F_5$, $F_6$, $F_7$, $F_8$, $F_9$, and X17 generational crosses with the recurrent parental line.

Quantitative Trait Loci (QTL). Quantitative trait loci (QTL) refer to genetic loci that control to some degree numerically representable traits that are usually continuously distributed.

Recombinant. As used herein, broadly describes various technologies whereby genes can be cloned, DNA can be sequenced, and protein products can be produced. As used herein, the term also describes proteins that have been produced following the transfer of genes into the cells of plant host systems.

Regeneration. Regeneration refers to the development of a plant from tissue culture.

Regulatory sequences. Refers to those sequences which are standard and known to those in the art that may be included in the expression vectors to increase and/or maximize transcription of a gene of interest or translation of the resulting RNA in a plant system. These include, but are not limited to, promoters, peptide export signal sequences, introns, polyadenylation, and transcription termination sites. Methods of modifying nucleic acid constructs to increase expression levels in plants are also generally known in the art (see, e.g. Rogers et al., 260 *J. Biol. Chem.* 3731-38, 1985; Cornejo et al., 23 *Plant Mol. Biol.* 567: 81,1993). In engineering a plant system to affect the rate of transcription of a protein, various factors known in the art, including regulatory sequences such as positively or negatively acting sequences, enhancers and silencers, as well as chromatin structure may have an impact. The present invention provides that at least one of these factors may be utilized in engineering plants to express a protein of interest. The regulatory sequences of the present invention are native genetic elements, i.e., are isolated from the selected plant species to be modified.

Selectable marker. A "selectable marker" is typically a gene that codes for a protein that confers some kind of resistance to an antibiotic, herbicide or toxic compound, and is used to identify transformation events. Examples of selectable markers include the streptomycin phosphotransferase (spt) gene encoding streptomycin resistance, the phosphomannose isomerase (pmi) gene that converts mannose-6-phosphate into fructose-6 phosphate; the neomycin phosphotransferase (nptII) gene encoding kanamycin and geneticin resistance, the hygromycin phosphotransferase (hpt or aphiv) gene encoding resistance to hygromycin, acetolactate synthase (als) genes encoding resistance to sulfonylurea-type herbicides, genes coding for resistance to herbicides which act to inhibit the action of glutamine synthase such as phosphinothricin or basta (e.g., the bar gene), or other similar genes known in the art.

Sense suppression. Reduction in expression of an endogenous gene by expression of one or more an additional copies of all or part of that gene in transgenic plants.

Specific gravity. As used herein, "specific gravity" is an expression of density and is a measurement of potato quality. There is a high correlation between the specific gravity of the tuber and the starch content and percentage of dry matter or total solids. A higher specific gravity contributes to higher recovery rate and better quality of the processed product.

T-DNA-Like. A "T-DNA-like" sequence is a nucleic acid that is isolated from a selected plant species, or from a plant that is sexually compatible with the selected plant species, and which shares at least 75%, 80%, 85%, 90%, or 95%, but not 100%, sequence identity with *Agrobacterium* species T-DNA. The T-DNA-like sequence may contain one or more border or border-like sequences that are each capable of integrating a nucleotide sequence into another polynucleotide.

Total Yield. Total yield refers to the total weight of all harvested tubers.

Trailer. Transcribed but not translated sequence following (or 3' to) a gene.

Transcribed DNA. DNA comprising both a gene and the untranslated leader and trailer sequence that are associated with that gene, which is transcribed as a single mRNA by the action of the preceding promoter.

Transformation of plant cells. A process by which DNA is stably integrated into the genome of a plant cell. "Stably" refers to the permanent, or non-transient retention and/or expression of a polynucleotide in and by a cell genome. Thus, a stably integrated polynucleotide is one that is a fixture within a transformed cell genome and can be replicated and propagated through successive progeny of the cell or resultant transformed plant. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols, viral infection, whiskers, electroporation, heat shock, lipofection, polyethylene glycol treatment, micro-injection, and particle bombardment.

Transgene. A gene that will be inserted into a host genome, comprising a protein coding region. In the context of the instant invention, the elements comprising the transgene are isolated from the host genome.

Transgenic plant. A genetically modified plant which contains at least one transgene.

Variant. A "variant," as used herein, is understood to mean a nucleotide or amino acid sequence that deviates from the standard, or given, nucleotide or amino acid sequence of a particular gene or protein. The terms, "isoform," "isotype," and "analog" also refer to "variant" forms of a nucleotide or an amino acid sequence. An amino acid sequence that is altered by the addition, removal or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "non-conservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software.

Vine Maturity. Vine maturity refers to a plant's ability to continue to utilize carbohydrates and photosynthesize. Vine maturity is scored on a scale of 1 to 5 where 1=dead vines and 5=vines green, still flowering.

The insertion of desirable traits into the genome of potato plants presents particular difficulties because potato is tetraploid, highly heterozygous and sensitive to in-breeding depression. It is therefore very difficult to efficiently develop transgenic potato plants that produce less acrylamide and less harmful Maillard-reaction products, including N-Nitroso-N-(3-keto-1,2-butanediol)-3'-nitrotyramine (Wang et al., Arch Toxicol 70: 10-5, 1995), 5-hydroxymethyl-2-furfural (Janzowski et al., Food Chem Toxicol 38: 801-9, 2000), and other Maillard reaction products with mutagenic properties (Shibamoto, Prog Clin Biol Res 304: 359-76, 1989), during processing using conventional breeding.

Several methods have been tested and research is ongoing to reduce acrylamide through process changes, reduction in dextrose, and additives such as asparaginase, citrate, and competing amino acids. The required capital expense to implement process changes throughout the potato industry would cost millions of dollars. In addition to the expense, these process changes have significant drawbacks including potentially negative flavors associated with additives such as asparaginase or citrate. Typically, fry manufacturers add dextrose during processing of french fries to develop the desired golden brown color, but dextrose also increases the formation of acrylamide through the Maillard reaction. Significant reductions in acrylamide occur by merely omitting dextrose from the process; however, the signature golden brown colors must then be developed some other way (such as though the addition of colors like annatto) The use of alternate colors, results in an absence of the typical flavors that develop through those browning reactions. Another challenge with the use of additives to reduce reactants like asparagine is moisture migration that occurs during frozen storage with the resulting return of asparagine to the surface and increased acrylamide. Finally, the blackening that occurs after potatoes are bruised affects quality and recovery in processing French fries and chips. Damaged and bruised potatoes must be trimmed or are rejected before processing, resulting in quality challenges or economic loss.

The "native technology" strategy of the present invention addresses the need of the potato industry to improve the agronomic characteristics and nutritional value of potatoes by reducing the expression of polyphenol oxidase-5 (PPO-5), which is responsible for black spot bruise, the expression of asparagine synthetase-1 (Asn-1), which is responsible for the accumulation of asparagine, a precursor in acrylamide formation, reducing the expression of the enzyme vacuolar invertase, which converts sucrose into glucose and fructose, and/or the expression of phosphorylase-L and kinase-R1, which are enzymes associated with the accumulation of reducing sugars that normally react with amino acids, such as asparagine, and form toxic Maillard products, including acrylamide. The partial or complete silencing of these genes in tubers decreases the potential to produce acrylamide. Use of the native technology of the invention allows for the incorporation of desirable traits into the genome of commercially valuable potato plant varieties by transforming the potatoes only with "native" genetic material, that is genetic material obtained from potato plants or plants that are sexually-compatible with potato plants, that contains only non-coding regulatory regions, without the integration of any foreign genetic material into the plant's genome. Desirable traits include high tolerance to impact-induced black spot bruise, increased resistance to late blight infection, reduced formation of the acrylamide precursor asparagine and reduced accumulation of reducing sugars, with consequent decrease in accumulation of toxic Maillard products, including acrylamide, improved quality and food color control. The incorporation of these desirable traits into existing potato varieties is impossible to achieve through traditional breeding because potato is tetraploid, highly heterozygous and sensitive to inbreeding depression.

The non-coding potato plant DNA insert sequences used in the present invention are native to the potato plant genome and do not contain any Agrobacterium DNA. One of the DNA inserts preferably comprises two expression cassettes and is inserted into a transformation vector referred to as the pSIM1278 transformation vector. The first cassette comprises fragments of both the asparagine synthetase-1 gene (Asn1) and the polyphenol oxidase-5 gene (Ppo5), arranged as inverted repeats between the Agp promoter of the ADP glucose pyrophosphorylase gene (Agp) and the Gbss promoter of the granule-bound synthase gene (Gbss). These promoters are predominantly active in tubers. The function of the second cassette is to silence the promoters of the starch associated gene dikinase-R1 (R1) and the phosphorylase-L gene (PhL). This cassette is comprised of fragments of the promoters of the starch associated gene dikinase-R1 (R1) and the phosphorylase-L gene (PhL), operably linked to the same Agp and Gbss promoters as the first cassette. These expression cassettes contain no foreign DNA, and consist of DNA only from either the selected plant species or from a plant that is sexually compatible with the selected plant species. A second DNA insert comes from the transformation vector referred to as pSIM1678 that comprises the Rpi-vnt1 expression cassette and a silencing cassette for the plant vacuolar invertase gene, VInv. The Rpi-vnt1 gene cassette consists of the VNT1 protein coding region regulated by its native promoter and terminator sequences to confer broad resistance to late blight, whereas the silencing cassette consists of an inverted repeat of sequence from the potato VInv gene flanked by opposing plant promoters, pGbss and pAgp. The function of the first cassette is to confer resistance to late blight, while the function of the second cassette is to silence the vacuolar invertase gene, reducing glucose and fructose.

The commercially valuable potato plant variety used in the present invention is Ranger Russet. Ranger Russet is the parent variety for X17. This full season variety was released in 1991. Ranger Russet is more resistant than Russet Burbank to Verticillium wilt, viruses X and Y, leafroll and net necrosis, and Fusarium dry rot. It is highly resistant to hollow heart. Plants are large and upright to spreading. Stems are thick, green that can be light brownish to light purple in full sun. Leaves are large, broad and medium green. Flowers are abundant and produce viable pollen. Buds are green with reddish-purple base and pedicel and moderate amount of short pubescence. Corolla is medium large, red-purple color and anthers are bright yellow. It produces high yields of good quality, high specific gravity tubers that are long and slightly flattened, and well suited for baking and processing into French fries. Tubers are susceptible to common scab and black spot bruise. Ranger Russet matures earlier than Russet Burbank and would be considered a medium-length storage variety. The variety is fertile and mainly grown in the Northwest, especially for the production of French fries.

The present invention provides a potato variety of significant market value—namely Ranger Russet—transformed with the transformation vector pSIM1278 followed by transformation with a second transformation vector pSIM1678, identified using the polymerase chain reaction rather than markers, and successfully propagated. Also provided are food products made from the tubers of the potato plant variety X17 of the present invention. Potato cultivar X17 has the following unique plant variety identifier with the Organization for Economic Cooperation and Development (OECD):

Targeted gene silencing with native DNA reduces the level of the RNA transcripts of the targeted genes in the tubers of the potato plant variety X17. Potato cultivar X17 contains expression cassettes that lower levels of reducing sugars in tubers by multiple mechanisms. Through the transformation with pSIM1278, silencing cassettes were introduced for the promoters of the starch associated gene (R1) and the phosphorylase-L gene (PhL), while transformation with pSIM1678 introduced a silencing cassette for the invertase gene (VInv; Ye et al., 2010). Together, these traits function by slowing the conversion of starch and sucrose to reducing sugars (glucose and fructose).

Thus, the tubers of the potato plant variety X17 of the invention incorporate highly desirable traits, including a reduced ratio in free amide amino acids asparagine and glutamine, which is associated with reduced acrylamide formation upon frying or baking. Specifically, the potato variety X17 of the present invention is characterized by two- to more than four-fold reduction in free-asparagine content, reduced discoloration associated with black spot bruise and increased resistance to late blight. Furthermore, the potato variety X17 of the invention displays a delay in the degradation of starch into the reducing sugars glucose and fructose during storage. Impairment of starch-to-sugar conversion further reduces senescence sweetening and acrylamide formation and limits heat-induced browning.

Potato variety X17 of the present invention is therefore extremely valuable in the potato industry and food market, as its tubers produce significantly less acrylamide upon heat processing and do not carry any potentially harmful foreign genes.

EXAMPLES

The present invention uses native technology to integrate native non-coding DNA into the genome of selected potato plant varieties to develop new intragenic potato plant varieties. The method includes trait identification, design of vectors, incorporation of vectors into *Agrobacterium*, selection of the recipient potato variety, plant transformation, evidence of absence of open reading frames, and confirmation that the new potato plant varieties contain only the native DNA. The potato cultivar X17 of the present invention has a lowered potential to form acrylamide, lower amounts of sucrose and is more resistant to black spot bruise than its untransformed counterpart. Additionally, potato cultivar X17 of the present invention has increased resistance to late blight.

Example 1

The pSIM1278 Transformation Vector Backbone

Plasmid pSIM1278 is a 19.7 kb binary transformation vector used to transform potatoes. This example shows the source of the genetic elements, the cloning steps for the backbone, and T-DNA sequences, and the order of the elements in the plasmid.

The plasmid backbone (FIG. 1 and Table 1) contains two well-characterized bacterial origins of replication. pVS1 (pVS1 Sta and Rep) enables maintenance of the plasmid in *Agrobacterium*, and pBR322 (pBR322 born and ori) enables maintenance of the plasmid in *Escherichia coli*. The *Agrobacterium* DNA overdrive sequence enhances cleavage at the RB, and the *E. coli*. nptII gene is a bacterial kanamycin selectable marker. The backbone contains an expression cassette comprising the *Agrobacterium* isopentenyl transferase (ipt) gene flanked by the Ranger Russet potato polyubiquitin (Ub17) promoter and the Ranger Russet potato polyubiquitin (Ub13) terminator. The ipt cassette is a screenable phenotype used to select against plasmid backbone DNA integration in the host plant. When present in transformed plant tissue, overexpression of ipt results in the overproduction of the plant hormone cytokinin resulting in plants with stunted phenotypes, abnormal leaves and the inability to root.

The backbone portion is not transferred into the plant cells. The various elements of the backbone are described in Table 1.

TABLE 1

Genetic Elements of the pSIM1278 Backbone

| Genetic Element | Origin | Accession Number[1] | Position | Size (bp) | Function |
| --- | --- | --- | --- | --- | --- |
| 1. Intervening sequence | Synthetic DNA | | 10,149-10,154 | 6 | Sequence used for cloning |
| 2. Overdrive | *Agrobacterium tumefaciens* Ti-plasmid | NC_002377 | 10,155-10,187 | 33 | Enhances cleavage of *A. tumefaciens* Right Border site[1] |
| 3. Intervening sequence | *Pseudomonas fluorescens* pVS1 | AJ537514 | 10,188-11,266 | 1,079 | pVS1 backbone[1] |
| 4. pVS1 partitioning protein StaA (PVS1 Sta) | *P. fluorescens* pVS1 | AJ537514 | 11,267-12,267 | 1,001 | pVS1 stability[1] |
| 5. Intervening sequence | *P. fluorescens* pVS1 | AJ537514 | 12,268-12,860 | 593 | pVS1 backbone[1] |
| 6. pVS1 replicon (pVS1Rep) | *P. fluorescens* pVS1 | AJ537514 | 12,861-13,861 | 1,001 | pVS1 replication region in *Agrobacterium*[1] |

TABLE 1-continued

Genetic Elements of the pSIM1278 Backbone

| Genetic Element | Origin | Accession Number[1] | Position | Size (bp) | Function |
|---|---|---|---|---|---|
| 7. Intervening sequence | P. fluorescens pVS1 | AJ537514 | 13,862-14,099 | 238 | pVS1 backbone[1] |
| 8. Intervening sequence | pBR322 | J01749 | 14,100-14,180 | 81 | pBR322 backbone[1] |
| 9. pBR322 bom | pBR322 | J01749 | 14,181-14,531 | 351 | pBR322 region for replication in E. coli[1] |
| 10. Intervening sequence | pBR322 | J01749 | 14,532-14,670 | 139 | pBR322 backbone[1] |
| 11. Origin of replication for pBR322 (pBR322 ori) | pBR322 | J01749 | 14,671-14,951 | 281 | Bacterial origin of replication[1] |
| 12. Intervening sequence | pBR322 | J01749 | 14,952-15,241 | 290 | pBR322 backbone[1] |
| 13. Neomycin phosphotransferase II (nptII) gene | Tn5 transposon | FJ362602 | 15,242-16,036 | 795 | Aminoglycoside phosphotransferase[1] (Simpson et al. 1985) |
| 14. Intervening sequence | Vector DNA | FJ362602 | 16,037-16,231 | 195 | pCAMBIA vector backbone[1] |
| 15. Terminator of the ubiquitin-3 gene (tUbi3) | S. tuberosum | GP755544 | 16,232-16,586 | 355 | Terminator for ipt gene transcription (Garbarino and Belknap, 1994) |
| 16. Intervening sequence | A. tumefaciens Ti-plasmid | NC_002377 | 16,587-16,937 | 351 | Sequence used for DNA cloning |
| 17. Isopentenyl transferase (ipt) gene | A. tumefaciens Ti-plasmid | NC_002377 | 16,938-17,660 | 723 | Condensation of AMP and isopentenyl-pyrophosphate to form isopentenyl-AMP, a cytokinin in the plant. Results in abnormal growth phenotypes in plant (Smigocki and Owens, 1988) |
| 18. Intervening sequence | Synthetic DNA | | 17,661-17,672 | 12 | Sequence used for DNA cloning |
| 19. Polyubiquitin promoter (Ubi7) | S. tuberosum var. Ranger Russet | U26831 | 17,673-19,410 | 1,738 | Promoter to drive expression of the ipt backbone marker gene (Garbarino et al., 1995) |
| 20. Intervening sequence | Vector DNA | U10460 | 19,411-19,660 | 250 | pZP200 vector backbone[1] |

[1]http://www.cambia.org/daisy/cambia/585.html - (General structure map of pCAMBIA vectors)

Example 2

The pSIM1278 Transformation Vector T-DNA

The pSIM1278 DNA insert region, including the flanking border sequences, used in the pSIM1278 is 10,148 bp long, from 1 bp to 10,148 bp. The pSIM1278 DNA insert consists of native DNA only and is stably integrated into the potato genome. The pSIM1278 DNA insert or a functional part thereof, is the only genetic material of vector pSIM1278 that is integrated in the potato plant varieties of the invention.

Figure 2:
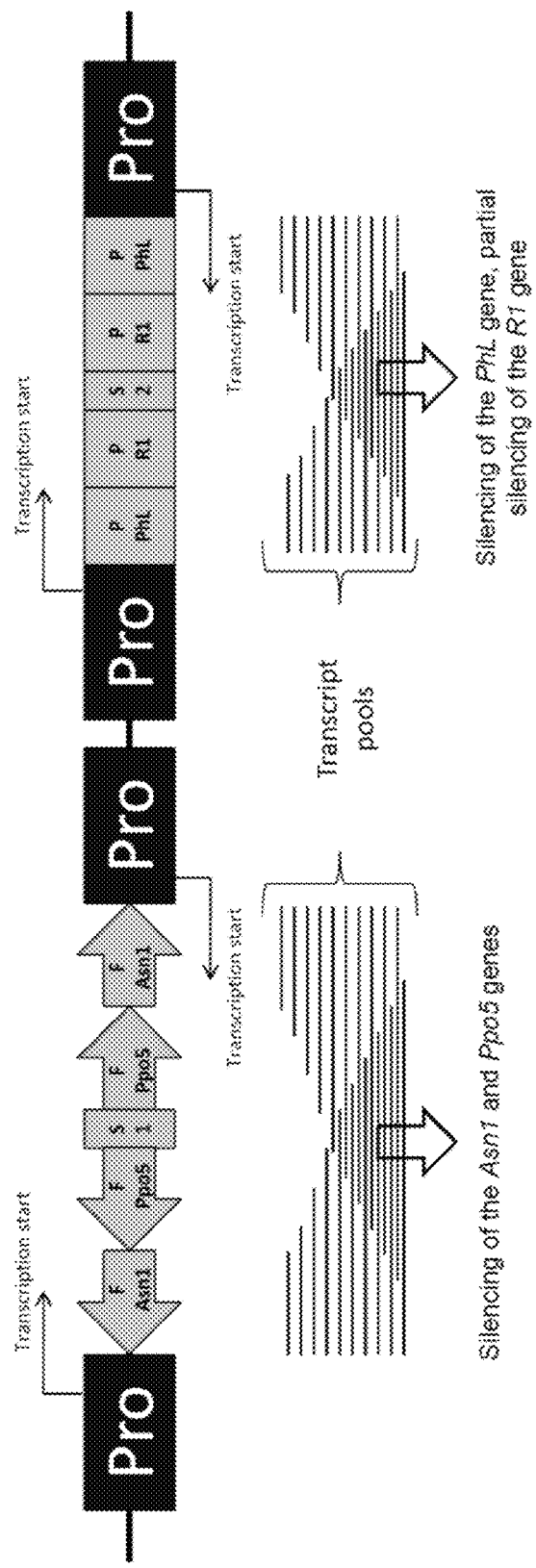
FIG. 2 provides a schematic representation of the silencing cassettes in the DNA insert inserted in the pSIM1278 transformation vector. Each silencing cassette contains two copies of two gene fragments separated by a spacer. Two copies of a DNA segment comprising fragments of four targeted genes, namely Asn-1, Ppo-5, Ph1 and R1, were inserted as inverted repeats between two convergent promoters, indicated as Pro, that are predominantly active in tubers. Plants containing the resulting silencing cassette produce a diverse and unpolyadenylated array of RNA molecules in tubers that dynamically and vigorously silence the intended target genes. The size of the RNA molecules was generally smaller than the distance between the two promoters employed because convergent transcription results in collisional transcription.

The pSIM1278 DNA insert is described in: FIG. 1 (along with vector backbone region), FIG. 2, and Table 2 below. The LB and RB sequences (25 bp each) were synthetically designed to be similar to and function like T-DNA borders from Agrobacterium tumefaciens. The GenBank Accession AY566555 was revised to clarify the sources of DNA for the Border regions. ASN1 described as genetic elements 5 and 10 is referred to as StAst1 in Chawla et al., 2012.

Plasmid pSIM1278 T-DNA Contains Two Expression Cassettes:

The first cassette (elements 4 to 12, Table 2) results in down-regulation of Asn1 and Ppo5 in the transformed potato variety. It is comprised of two identical 405 bp fragments of Asn1 and two identical 144 bp fragments of Ppo5. The fragments of Asn1 and Ppo5 are arranged as inverted repeats separated by a non-coding 157 bp Ranger Russet potato nucleotide spacer element. The Asn1 and Ppo5 fragments are arranged between the two convergent potato promoters; the Agp promoter of the ADP glucose pyrophosphorylase gene (Agp) and the Gbss promoter of the granule-bound starch synthase gene (Gbss) that are primarily active in tubers. These promoters drive expression of the inverted repeats to generate double-stranded RNA and down-regulate Asn1 and Ppo5.

The second cassette (elements 14 to 21, Table 2) results in down-regulation of PhL and R1 in the transformed potato variety. It is comprised of two identical 509 bp fragments of the PhL promoter region (pPhL) and two identical 532 bp fragments of R1 promoter region (pR1). The pPhL and pR1 fragments are arranged as inverted repeats separated by a non-coding 258 bp fragment of the Ranger Russet potato polyubiquitin gene. Like the first cassette, the pPhL and pR1 fragments are arranged between and transcribed by the potato Agp and Gbss promoters.

TABLE 2

Genetic Elements of pSIM1278 T-DNA, from Left Border Site to Right Border

| Genetic Element | Origin | Accession Number | Position (pSIM1278) | Size (bp) | Intended Function |
|---|---|---|---|---|---|
| 1. Left Border (LB) site[1] | Synthetic | AY566555[5] (bases 1-25) | 1-25 | 25 | Site for secondary cleavage to release single-stranded DNA insert from pSIM1278 (van Haaren et al. 1989) |
| 2. Left Border region sequence including LB | S. tuberosum var. Ranger Russet. | AY566555[5] (bases 26-187) | 26-187 | 162 | Supports secondary cleavage at LB |
| 3. Intervening Sequence | S. tuberosum | AF393847 | 188-193 | 6 | Sequence used for DNA cloning |

TABLE 2-continued

Genetic Elements of pSIM1278 T-DNA, from Left Border Site to Right Border

| Genetic Element | Origin | Accession Number | Position (pSIM1278) | Size (bp) | Intended Function |
|---|---|---|---|---|---|
| 4. Promoter for the ADP glucose pyrophosphorylase gene (pAgp), 1st copy | S. tuberosum var. Ranger Russet | HM363752 | 194-2,453 | 2260 | One of the two convergent promoters that drives expression of an inverted repeat containing fragments of Asn1 and Ppo5, especially in tubers |
| 5. Fragment of the asparagine synthetase-1 (Asn1) gene (1st copy antisense orientation) | S. tuberosum var. Ranger Russet | HM363759 | 2,454-2,858 | 405 | Generates with (10) double stranded RNA that triggers the degradation of Asn1 transcripts to impair asparagine formation (Chawla et al., 2012[2]) |
| 6. 3'-untranslated sequence of the polyphenol oxidase-5 gene (Ppo5) (1st copy, in antisense orientation) | S. verrucosum | HM363754 | 2,859-3,002 | 144 | Generates with (9) double stranded RNA that triggers the degradation of Ppo5 transcripts to block black spot development |
| 7. Intervening Sequence | S. tuberosum | DQ478950 | 3,003-3,008 | 6 | Sequence used for DNA cloning |
| 8. Spacer-1 | S. tuberosum var. Ranger Russet | HM363753 | 3,009-3,165 | 157 | Sequence between the 1st inverted repeats |
| 9. 3'-untranslated sequence of the polyphenol oxidase-5 gene (Ppo5) (2nd copy, in sense orientation) | S. verrucosum | HM363754 | 3,166-3,309 | 144 | Generates with (6) double stranded RNA that triggers the degradation of Ppo5 transcripts to block black spot development |
| 10. Fragment of the asparagine synthetase-1 (Asn1) gene (2nd copy, in sense orientation) | S. tuberosum var. Ranger Russet | HM363759 | 3,310-3,715 | 406 | Generates with (5) double stranded RNA that triggers the degradation of Asn1 transcripts to impair asparagine formation (Chawla et al., 2012[2]) |
| 11. Intervening Sequence | S. tuberosum | X73477 | 3,716-3,721 | 6 | Sequence used for DNA cloning |
| 12. Promoter for the granule-bound starch synthase (pGbss) gene (1st copy, convergent orientation relative to the 1st copy of pAgp) | S. tuberosum var. Ranger Russet | HM363755 | 3,722-4,407 | 686 | One of the two convergent promoters that drives expression of an inverted repeat containing fragments of Asn1 and Ppo5, especially in tubers |
| 13. Intervening Sequence | S. tuberosum | X95996/ AF393847 | 4,408-4,423 | 16 | Sequence used for DNA cloning |
| 14. pAgp, 2nd copy | S. tuberosum var. Ranger Russet | HM363752 | 4,424-6,683 | 2260 | One of the two convergent promoters that drives expression of an inverted repeat containing fragments of the promoters of PhL and R1, especially in tubers |
| 15. Fragment of promoter for the potato phosphorylase-L (pPhL) gene (1st copy, in antisense orientation) | S. tuberosum var. Ranger Russet | HM363758 | 6,684-7,192 | 509 | Generates with (20) double stranded RNA that triggers the degradation of PhL transcripts to limit the formation of reducing sugars through starch degradation |
| 16. Fragment of promoter for the potato R1 gene (pR1) (1st copy, in antisense orientation) | S. tuberosum var. Ranger Russet | HM363757 | 7,193-7,724 | 532 | Generates with (19) double stranded RNA that triggers the degradation of R1 transcripts to limit the formation of reducing sugars through starch degradation |
| 17. Intervening Sequence | S. tuberosum | DQ478950 | 7,725-7,730 | 6 | Sequence used for DNA cloning |
| 18. Spacer-2 | S. tuberosum var. Ranger Russet | U26831[3] | 7,731-7,988 | 258 | Sequence between the 2nd inverted repeat |
| 19. Fragment of promoter for the potato R1 gene (pR1) (2nd copy, in sense orientation) | S. tuberosum var. Ranger Russet | HM363757 | 7,989-8,520 | 532 | Generates with (16) double stranded RNA that triggers the degradation of R1 transcripts to limit the formation of reducing sugars through starch degradation |
| 20. Fragment of promoter for the potato phosphorylase-L (pPhL) gene (2nd copy, in sense orientation) | S. tuberosum var. Ranger Russet | HM363758 | 8,521-9,029 | 509 | Generates with (15) double stranded RNA that triggers the degradation of PhL transcript to limit the formation of reducing sugars through starch degradation |
| 21. pGbss (2nd copy, convergent orientation relative to the 2nd copy of pAgp) | S. tuberosum var. Ranger Russet | X83220[4] | 9,030-9,953 | 924 | One of the two convergent promoters that drives expression of an inverted repeat containing fragments of the promoters of PhL and R1, especially in tubers |
| 22. Intervening Sequence | S. tuberosum | AF143202 | 9,954-9,962 | 9 | Sequence used for DNA cloning |
| 23. Right Border region sequence including RB | S. tuberosum var. Ranger Russet | AY566555[5] (bases 231-391) | 9,963-10,123 | 161 | Supports primary cleavage at RB-Like site |

TABLE 2-continued

Genetic Elements of pSIM1278 T-DNA, from Left Border Site to Right Border

| Genetic Element | Origin | Accession Number | Position (pSIM1278) | Size (bp) | Intended Function |
|---|---|---|---|---|---|
| 24. Right Border (RB) sequence[1] | Synthetic | AY566555[5] (bases 392-416) | 10,124-10,148 | 25 | Site for primary cleavage to release single stranded DNA insert from pSIM1278 (van Haaren et al. 1989) |

[1]The LB and RB sequences (25-bp each) were synthetically designed to be similar to and function like T-DNA borders from *Agrobacterium tumefaciens*.
[2]ASN1 described as genetic elements 5 and 11 is referred to as StAst1 in Chawla et al. 2012.
[3]GenBank Accession HM363756 is replaced with a citation to GenBank Accession U26831 to properly include four 3' end nucleotides present in the pGbss DNA element of the pSIM1278 construct.
[4]GenBank Accession HM363755 is replaced with a citation to GenBank Accession X83220 to properly include the full pGbss (2nd copy) DNA insert sequence present in the pSIM1278 construct.
[5]GenBank Accession AY566555 was revised to clarify the sources of DNA for the Border regions.

Thus, as can be seen from Table 1 and Table 2, the pSIM1278 plasmid is a binary vector designed for potato plant transformation. The vector backbone contains sequences for replication in both *E. coli* and *Agrobacterium* along with an ipt marker for screening to eliminate plants with vector backbone DNA. The T-DNA region consists of two expression cassettes flanked by LB and RB sequences. Upon inoculation of host plant tissue with *Agrobacterium* containing the pSIM1278 vector, the T-DNA region of pSIM1278 is transferred into the host genome.

The DNA insert described in Table 2 that was used to create potato cultivar X17 of the present disclosure does not activate adjacent genes and does not adversely affect the phenotype of potato plant varieties.

Example 3

The pSIM1678 Transformation Vector Backbone

Plasmid pSIM1678 is a 18.6 kb binary transformation vector used to transform potatoes. This example shows the source of the genetic elements, the cloning steps for the backbone, and T-DNA sequences, and the order of the elements in the plasmid.

Figure 3:
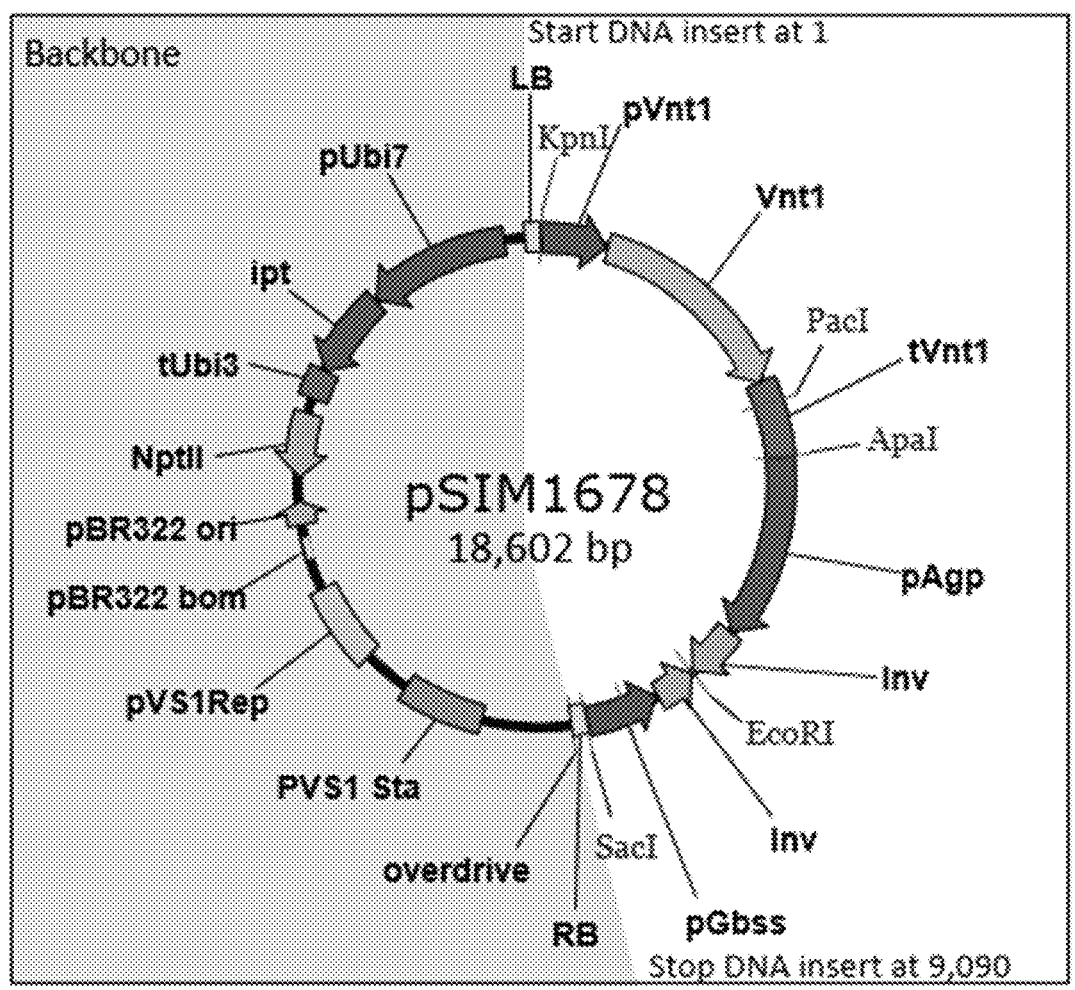
FIG. 3 depicts the pSIM1678 transformation vector of the present invention. The vector backbone region, on the left, is 9,512 bp long, as it starts at position 9,091 bp and ends at position 18,602 bp. The backbone DNA consists mainly of bacterial DNA which provides support maintenance of the DNA insert prior to plant transformation. The DNA insert region (right side), including flanking Border sequences, is 9,090 bp long (from 1 bp to 9,090 bp). The DNA insert consists of native DNA only and was stably integrated into the potato genome upon transformation.

The plasmid backbone (FIG. 3; Table 3) contains two well-characterized bacterial origins of replication. pVS1 (pVS1 Sta and Rep) enables maintenance of the plasmid in *Agrobacterium*, and pBR322 (pBR322 bom and ori) enables maintenance of the plasmid in *Escherichia coli*. The *Agrobacterium* DNA overdrive sequence enhances cleavage at the RB, and the *E. coli*. nptII gene is a bacterial kanamycin selectable marker. The backbone contains an expression cassette comprising the *Agrobacterium* isopentenyl transferase (ipt) gene flanked by the Ranger Russet potato polyubiquitin (Ubi7) promoter and the Ranger Russet potato polyubiquitin (Ubi3) terminator (Garbarino and Belknap, 1994). The ipt cassette is a screenable phenotype used to select against plasmid backbone DNA integration in the host plant. When present in transformed plant tissue, overexpression of ipt results in the overproduction of the plant hormone cytokinin resulting in plants with stunted phenotypes, abnormal leaves and the inability to root.

The backbone portion is not transferred into the plant cells. The various elements of the backbone are described in Table 3.

TABLE 3

Genetic Elements of the pSIM1678 Backbone

| Genetic Element | Origin | Accession Number[1] | Position | Size (bp) | Function[1] http://www.cambia.org/daisy/cambia/585.html - (General structure map of pCAMBIA vectors) |
|---|---|---|---|---|---|
| 1. Intervening sequence | Synthetic DNA | | 9,091-9,096 | 6 | Sequence used for cloning |
| 2. Overdrive | *Agrobacterium tumefaciens* Ti-plasmid | NC_002377 | 9,097-9,126 | 30 | Enhances cleavage of *A. tumefaciens* Right Border site[1] |
| 3. Intervening sequence | *Pseudomonas fluorescens* pVS1 | AJ537514 | 9,127-10,208 | 1,082 | pVS1 backbone[1] |
| 4. pVS1 partitioning protein StaA (PVS1 Sta) | *P. fluorescens* pVS1 | AJ537514 | 10,209-11,209 | 1,001 | pVS1 stability[1] |
| 5. Intervening sequence | *P. fluorescens* pVS1 | AJ537514 | 11,210-11,802 | 593 | pVS1 backbone[1] |
| 6. pVS1 replicon (pVS1Rep) | *P. fluorescens* pVS1 | AJ537514 | 11,803-12,803 | 1,001 | pVS1 replication region in *Agrobacterium*[1] |
| 7. Intervening sequence | *P. fluorescens* pVS1 | AJ537514 | 12,804-13,040 | 237 | pVS1 backbone[1] |
| 8. Intervening sequence | pBR322 | J01749 | 13,041-13,212 | 172 | pBR322 backbone[1] |
| 9. pBR322 bom | pBR322 | J01749 | 13,213-13,473 | 261 | pBR322 region for replication in *E. coli*[1] |
| 10. Intervening sequence | pBR322 | J01749 | 13,474-13,612 | 139 | pBR322 backbone[1] |
| 11. Origin of replication for pBR322 (pBR322 ori) | pBR322 | J01749 | 13,613-13,893 | 281 | Bacterial origin of replication[1] |
| 12. Intervening sequence | pBR322 | J01749 | 13,894-14,183 | 290 | pBR322 backbone[1] |
| 13. Neomycin phosphotransferase II (nptII) gene | Tn5 transposon | FJ362602 | 14,184-14,978 | 795 | Aminoglycoside phosphotransferase[1] (Simpson et al. 1985) |
| 14. Intervening sequence | Vector DNA | FJ362602 | 14,979-15,173 | 195 | pCAMBIA vector backbone[1] |

TABLE 3-continued

Genetic Elements of the pSIM1678 Backbone

| Genetic Element | Origin | Accession Number[1] | Position | Size (bp) | Function[1] http://www.cambia.org/daisy/cambia/585.html - (General structure map of pCAMBIA vectors) |
|---|---|---|---|---|---|
| 15. Terminator of the ubiquitin-3 gene (tUbi3) | S. tuberosum | GP755544 | 15,174-15,528 | 355 | Terminator for ipt gene transcription (Garbarino and Belknap, 1994) |
| 16. Intervening sequence | A. tumefaciens Ti-plasmid | NC_002377 | 15,529-15,879 | 351 | Sequence used for DNA cloning |
| 17. Isopentenyl transferase (ipt) gene | A. tumefaciens Ti-plasmid | NC_002377 | 15,880-16,602 | 723 | Condensation of AMP and isopentenyl-pyrophosphate to form isopentenyl-AMP, a cytokinin in the plant. Results in abnormal growth phenotypes in plant (Smigocki and Owens, 1988) |
| 18. Intervening sequence | Synthetic DNA |  | 16,603-16,614 | 12 | Sequence used for DNA cloning |
| 19. Polyubiquitin promoter (Ubi7) | S. tuberosum var. Ranger Russet | (A )U26831 | 16,615-18,352 | 1,738 | Promoter to drive expression of the ipt backbone marker gene (Garbarino et al., 1995) |
| 20. Intervening sequence | Vector DNA | (B) U10460 | 18,353-18,602 | 250 | pZP200 vector backbone |

Example 4

The pSIM1678 Transformation Vector T-DNA

The pSIM1678 DNA insert region, including the flanking border sequences, used in the pSIM1678 is 9,090 bp long (from 1 bp to 9,090 bp). The pSIM1678 DNA insert consists of native DNA only and is stably integrated into the potato genome. The pSIM1678 DNA insert or a functional part thereof, is the only genetic material of vector pSIM1678 that is integrated in the potato plant varieties of the invention.

The pSIM1678 DNA insert is described in FIG. 3 (along with vector backbone region) and Table 4 below. In Table 4, the LB and RB sequences (25-bp each) were synthetically designed to be similar to and function like T-DNA borders from *Agrobacterium tumefaciens*. GenBank Accession AY566555 was revised to clarify the sources of DNA for the Border regions.

Plasmid pSIM1678 T-DNA is from 1-bp to 9,090-bp and contains two expression cassettes (FIG. 3):

The first cassette (elements 4 to 6, Table 4) contains the 2,626 bp Rpi-vnt1 (Vnt1) gene originating from *Solanum venturii*. The gene product, VNT1, is an R-protein involved in the plant immune response that protects potato from late blight infection from *Phytophthora infestans*. The gene is expressed under the native Vnt1 promoter, pVnt1, and terminator, tVnt1.

The second cassette (elements 8 to 14, Table 4) results in down-regulation of vaculor Invertase (VInv) in the transformed potato variety. It is comprised of two fragments of VInv (elements 10 and 12, Table 4) arranged as inverted repeats separated. VInv fragments are arranged between the two convergent potato promters; the Agp promoter of the ADP glucose pyrophosphorylase gene (Agp) and the Gbss promoter of the granule-bound starch synthase gene (Gbss) that are primarily active in tubers. These promoters drive expression of the inverted repeats to generate double-stranded RNA and down-regulate VInv.

TABLE 4

Genetic Elements of pSIM1678 T-DNA, from Left Border Site to Right Border

| Genetic Element | Origin | Accession Number | Position (pSIM1678) | Size (bp) | Intended Function |
|---|---|---|---|---|---|
| 1. Left Border (LB) site[1] | Synthetic | AY566555[3] (bases 1-25) | 1-25 | 25 | Site for secondary cleavage to release single-stranded DNA insert from pSIM1678 |
| 2. Left Border region sequence including LB | S. tuberosum var. Ranger Russet. | AY566555[3] (bases 1-187) | 26-187 | 162 | Supports secondary cleavage at LB |
| 3. Intervening Sequence | S. tuberosum | AF393847 | 188-193 | 6 | Sequence used for DNA cloning |
| 4. Native promoter for the late blight resistance gene (Vnt1) | S. venturii | FJ423044 | 194-902 | 709 | Drives expression of late blight resistance gene vnt1 |
| 5. Late blight resistance gene VNt1 (Rpi-vnt1) | S. venturii | FJ423044 | 903-3,578 | 2676 | *Solanum venturii* late blight resistance protein gene |
| 6. Native terminator for the Vnt1 gene | S. venturii | FJ423044 | 3,579-4,503 | 925 | Ends transcription of late blight resistance gene vnt1 |
| 7. Intervening Sequence | S. tuberosumt | HM363755 | 4,504-4,510 | 7 | Sequence used for DNA cloning |
| 8. Promoter for the ADP glucose pyrophosphorylase gene (pAgp) | S. tuberosum var. Ranger Russet | HM363752 | 4,511-6,770 | 2260 | One of the two convergent promoters that drives expression of an inverted repeat containing fragments of acid invertase gene |
| 9. Intervening Sequence | S. tuberosum var. Ranger Russet | DQ206630 | 6,771-6,776 | 6 | Sequence used for DNA cloning |

TABLE 4-continued

Genetic Elements of pSIM1678 T-DNA, from Left Border Site to Right Border

| Genetic Element | Origin | Accession Number | Position (pSIM1678) | Size (bp) | Intended Function |
|---|---|---|---|---|---|
| 10. Fragment of the acid invertase (Inv) (sense orientation) | S. tuberosum var. Ranger Russet | DQ478950 | 6,777-7,455 | 679 | Generates with (12) double stranded RNA that triggers the degradation of invertase transcripts |
| 11. Intervening Sequence | S. tuberosum var. Ranger Russet | X73477 | 7,456-7,461 | 6 | Sequence used for DNA cloning |
| 12. Fragment of the acid invertase (Inv) (anti-sense orientation) | S. tuberosum var. Ranger Russet | DQ478950 | 7,462-7,965 | 504 | Generates with (10) double stranded RNA that triggers the degradation of invertase transcripts |
| 13. Intervening Sequence | S. tuberosum var. Ranger Russet | X95996 | 7,966-7,971 | 6 | Sequence used for DNA cloning |
| 14. Promoter for the granule-bound starch synthase (pGbss) gene (convergent orientation relative to the pAgp) | S. tuberosum var. Ranger Russet | X83220[2] | 7,972-8,895 | 924 | One of the two convergent promoters that drives expression of an inverted repeat containing fragments of invertase gene, especially in tubers |
| 15. Intervening Sequence | S. tuberosum | AF143202 | 8,896-8904 | 9 | Sequence used for DNA cloning |
| 16. Right Border region sequence including RB | S. tuberosum var. Ranger Russet | AY566555[3] (bases 231-416) | 8905-9,065 | 161 | Supports primary cleavage at RB-Like site |
| 17. Right Border (RB) sequence[1] | Synthetic | AY566555[3] (bases 392-416) | 9,066-9,090 | 25 | Site for primary cleavage to release single stranded DNA insert from pSIM1678 (van Haaren et al., 1989) |

[1]The LB and RB sequences (25-bp each) were synthetically designed to be similar to and function like T-DNA borders from Agrobacterium tumefaciens.
[2]GenBank Accession HM363755 is replaced with a citation to GenBank Accession X83220 to properly include the full pGbss (2nd copy) DNA insert sequence present in the pSIM1278 construct.
[3]GenBank Accession AY566555 was revised to clarify the sources of DNA for the Border regions.

Thus, as can be seen from Table 3 and Table 4, the pSIM1678 plasmid is a binary vector designed for potato plant transformation. The vector backbone contains sequences for replication in both *E. coli* and *Agrobacterium* along with an ipt marker for screening to eliminate plants with vector backbone DNA. The T-DNA region consists of two expression cassettes flanked by LB and RB sequences. Upon inoculation of host plant tissue with *Agrobacterium* harboring the pSIM1678 vector, the T-DNA region of pSIM1678 is transferred into the host genome.

Example 5

The *Agrobacterium* Strain and Transfection

The C58-derived *Agrobacterium* strain AGL1 was developed by precisely deleting the transfer DNA of the hyper-virulent plasmid pTiBo542 (Lazo et al., 1991). A transposon insertion in the general recombination gene (recA) stabilizes recombinant plasmid vectors such as pSIM1278 (FIG. 1). AGL1 displays resistance against carbenicillin and rifampicin, and is eliminated from transformed potato tissue using timentin. Following selection, plants are both antibiotic and *Agrobacterium* free, with the potato-derived expression cassettes inserted into the plant's genome.

Stock plants were maintained in magenta boxes with 40 ml half-strength M516 (Phytotechnology) medium containing 3% sucrose and 2 g/l gelrite (propagation medium). Potato internode segments of four to six mm were cut from four-week old plants, infected with the *Agrobacterium* AGL1 strain carrying pSIM1278, and transferred to tissue culture media containing 3% sucrose and 6 g/l agar (co-cultivation medium). Infected explants were transferred, after two days, to M404 (Phytotechnology) medium containing 3% sucrose, 6 g/l agar and 150 mg/l timentin to eliminate *Agrobacterium* (hormone-free medium). Details of the methods are described in Richael et al. (2008).

After one month, the infected explants were transferred to fresh medium lacking any synthetic hormones and incubated in a Percival growth chamber under a 16 hr photoperiod at 24° C. where they started to form shoots. Many shoots expressed the ipt gene and displayed a cytokinin overproduction phenotype; these shoots were not considered for further analyses. PCR genotyping demonstrated that about 0.3 to 1.5% of the remaining shoots contained at least part of the P-DNA while lacking the ipt gene. Thus, no markers were used to select for the transformed plants. Details on ipt-based marker-free plant transformation were published by Richael et al. (2008).

The process of eliminating *Agrobacterium* started two days after explant infection. For this purpose, tissues were subjected to the antibiotic timentin (150 mg/L) until proven to be free of live *Agrobacterium*. Proof was obtained by incubating stem fragments of transformed events on nutrient broth-yeast extract (NBY medium) for 2 weeks at 28° C. (repeated twice). In accordance with 97 CFR Part 340, transformed plants were transported and planted in the field only when free of live *Agrobacterium*.

The Ranger Russet X17 event contains inserts derived from two separate transformations with different plasmids. The first insert, plasmid pSIM1278, contains two cassettes consisting of inverted repeats designed to silence up to four potato genes, Asn1, Ppo5, R1, and PhL, in tubers. Similarly, the second plasmid, pSIM1678, contains a cassette consisting of an inverted repeat to silence the VInv gene in tubers, while also containing a copy of the Rpi-vnt1 gene under its native potato promoter.

Potato plant varieties were analyzed by DNA gel blot analyses to determine the structure and copy number of integrated DNA insert sequences and to confirm the absence of vector backbone sequences.

Example 6

Evidence for the Absence of the Vector Backbone DNA

Unlike many commercial transgenic crops, potato cultivars of the disclosure were confirmed to be free of *Agrobacterium*-derived DNA sequences that are used for transformation, such as vector backbone DNA, by two different methods: 1) First, the presence or absence of the negative selectable isopentenyl isomerase (ipt) marker gene in the vector backbone was determined, as inadvertent transfer of backbone DNA comprising the ipt gene expression cassette from *Agrobacterium* to plant cells would trigger ipt gene expression and, consequently, the formation of the cytokinin-type hormone isopentenyladenosine, if plants had phenotypes associated with the negative selectable isopentenyl isomerase (ipt) marker gene in the plasmid backbone, they were discarded; and 2) Southern blot hybridization was then used on the transformed potato plants that had passed the first screening method to confirm the absence of backbone DNA.

Thus, the above two analyses have shown that the Ranger Russet X17 event does not contain backbone from either plasmid used in the transformations.

Example 7

Stability of the Inserted DNA

Bacterial T-DNAs are not always stable after insertion into a plant. The estimated instability rate ($0.5$-$5.9 \times 10^{-4}$) is associated with meiosis (Müllner et al. 1987; Conner et al. 1998), which is not relevant to potatoes as they reproduce vegetatively. Thus, DNA insertions are expected to be stable. Tubers rather than seeds were used to define subsequent generations since tubers are what are commercially planted.

Genetic stability was assessed using both molecular and phenotypic assays. The structure of the insert was shown to be stable using Southern blot analysis of genomic DNA isolated over three generations of X17 potatoes (G0-G3), whereas the phenotypic stability was assessed by measuring polyphenol oxidase activity, in the second generation of field-grown tubers. This method shows visual evidence of PPO silencing after applying catechol to the cut surface of potatoes. These studies were carried out to ensure that the desired genetic changes in X17 remained stable over multiple clonal cycles while maintaining the traits.

The stability of the DNA inserts was evaluated by comparing three successive clonal generations (G1, G2, and G3) to the original transformant (G0) using Southern blots. Stable DNA inserts are expected to maintain the same structure and thus produce the same digestion patterns over multiple generations of the plant. To test stability of the inserts in the X17 event, its digestion pattern was compared using two probes (GBS1 and AGP) that hybridize to regions of the inserts from both pSIM1278 and pSIM1678, and two probes (INV and VNT1) that are specific to the pSIM1678 insert. Since the DNA sequences these probes hybridize with are contained in the potato genome as well as within the DNA insert(s), both endogenous and insert-specific bands are expected in the Southern blots.

All genomic DNA samples were digested with the restriction enzyme, EcoRV, and hybridized with a probe specific to either AGP or GBS1. EcoRV was chosen for these studies as it digests within both inserts to provide a unique banding pattern with internal bands of predicted size in the pSIM1278 insert (e.g. 2.3 kb). The banding patterns between all samples of X17 were identical to each other for both probes. The multiple bands present in the Ranger Russet control are also found in X17, but X17 also contains bands corresponding to the pSIM1278 and pSIM1678 inserts. These bands are similarly consistent between all generations of X17 analyzed indicating genetic stability of both inserts.

A second analysis was performed using two probes specific to the pSIM1678 insert. For this analysis, genomic DNA samples were digested with the restriction enzyme, XbaI, and hybridized with VNT1 and INV probes. XbaI was chosen as the restriction enzyme for these studies as it digests the pSIM1678 internally and produces a band of known size (e.g. 4.6 kb for the INV probe). Again, both endogenous and insert-specific bands were detected with consistent banding patterns between the three generations analyzed. The genetic and phenotypic analyses indicated the insertions arising from transformation of both pSIM1278 and pSIM1678 are stable over three generations. Given the demonstrated stability over three generations, it is likely that stability will be maintained during subsequent cycles of vegetative propagation.

Example 8

Efficacy and Tissue-Specificity of Gene Silencing

Figure 4:
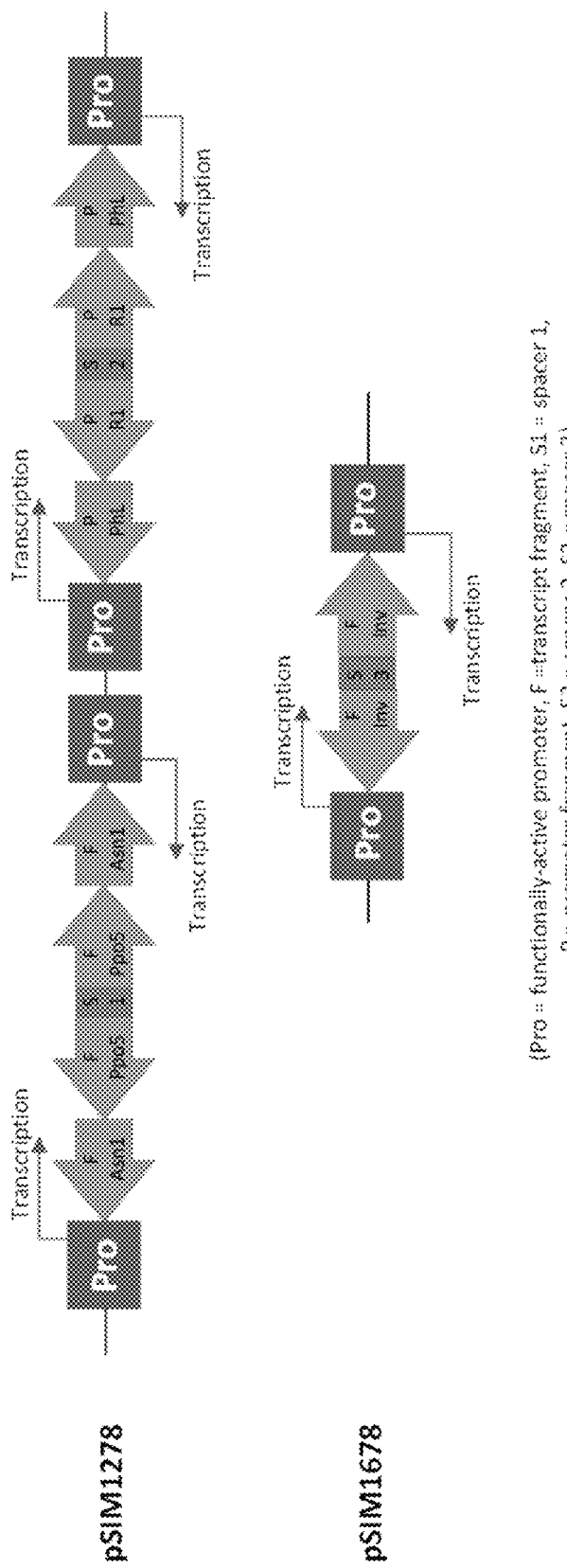
FIG. 4 provides a schematic representation of the silencing cassettes in the DNA insert inserted in the pSIM1278 transformation vector (upper construct) and the silencing cassette in the DNA insert inserted in the pSIM1678 transformation vector (lower construct)
Figure 5:
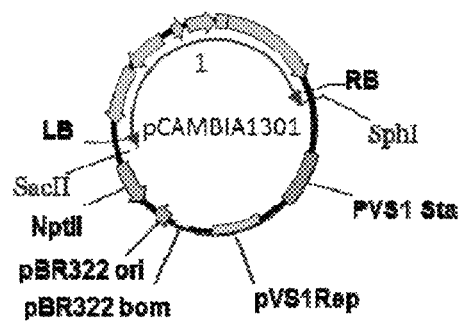
FIG. 5 illustrates the process for constructing plasmid pSIM1278, utilizing the DNA sequences as described in Table 1 and Table 2. The starting vector, pCAMBIA1301, contains the origins of replications in the final pSIM1278 backbone. 1) Deleted T-DNA region between the SacII and SphI restriction sites of pCAMBIA1301. 2) Inserted new T-DNA region between the SacII and SphI restriction sites adding KpnI and SacI restriction sites. 3) Inserted ipt cassette (pUbi7, ipt, tUbi3) into SacII restriction site. 4) Deleted DNA between KpnI and SacI. Inserted T-DNA region assembled from potato DNA sequence (FIG. 6) into KpnI and SacI.
Figure 5:
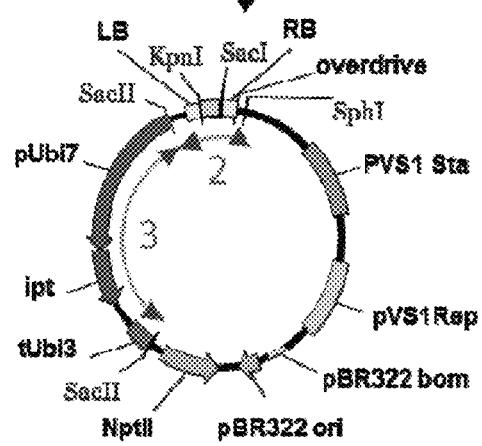
Figure 5:
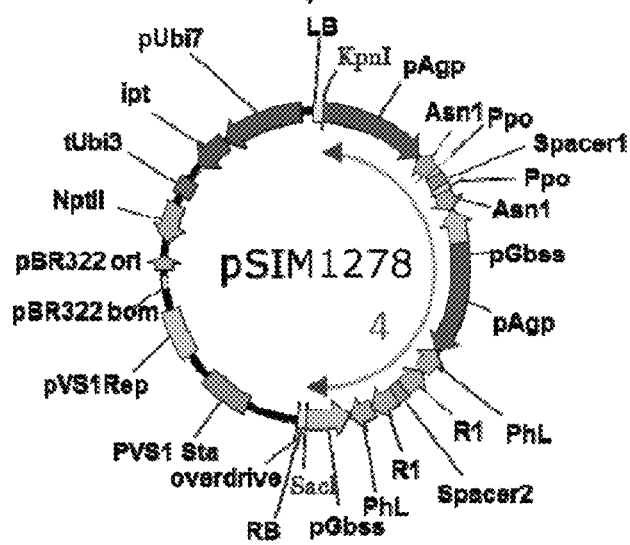
Figure 6:
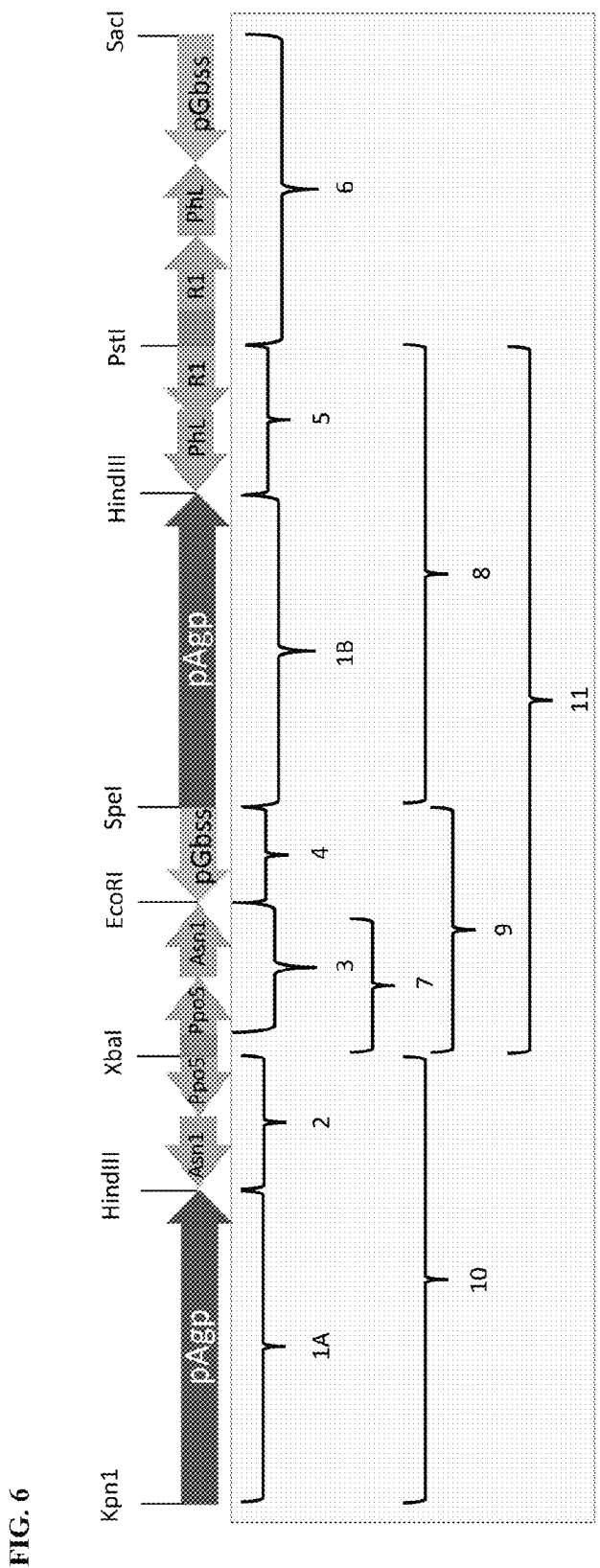
FIG. 6 illustrates the construction of T-DNA expression cassettes in pSIM1278. Fusion PCR was used to amplify elements 1A (pAgp—1st copy), 1B (pAgp-2nd copy), 2 (Asn1, Ppo5), 3 (Ppo5, Asn1), 4 (pGbss—1st copy) and 7 (Spacer1, Ppo5, Asn1). Elements 5 (PhL, R1) and 6 (Spacer2, R1, PhL, pGbss) were synthesized by the Blue Heron Biotechnology, Inc. (Bothell, Wash.) based on the sequence from the potato genome. Elements 8, 9, and 10 were generated by ligating building blocks shown in the figure. In the end, three fragments, 10, 11 and 6 were created to span the desired expression cassette. These three fragments were ligated and inserted into the KpnI-SacI restriction sites shown in FIG. 5 to generate pSIM1278.
Figure 7:
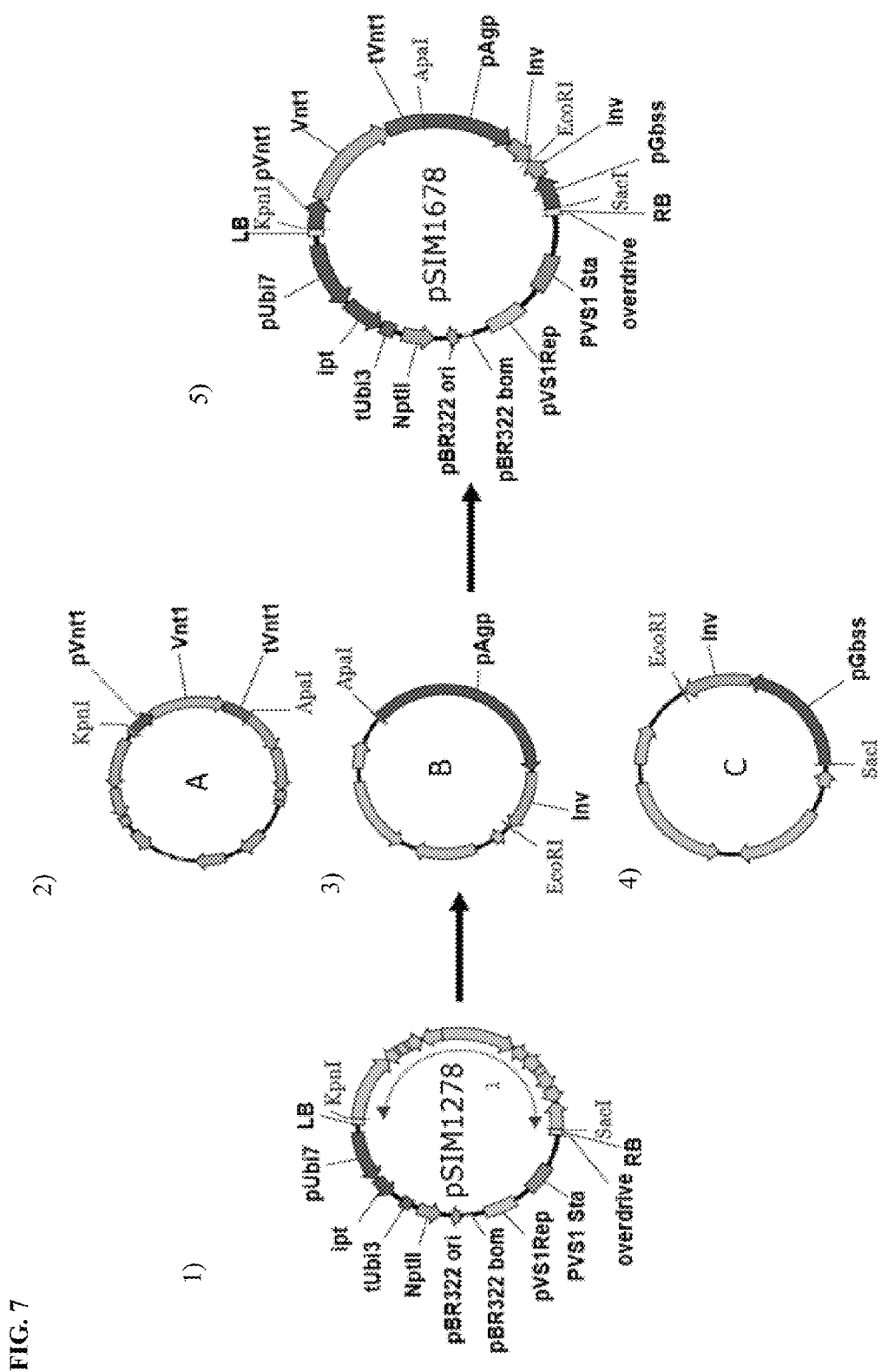
FIG. 7 illustrates the process for constructing plasmid pSIM1678, utilizing the DNA sequences as described in Table 3 and Table 4. The starting vector, pSIM1278, contains the final pSIM1678 backbone. 1) Deleted T-DNA region between the KpnI and SacI restriction sites of pSIM1278. 2) Inserted PCR amplified pVnt1, Vnt1 and tVnt1 into construct A with flanking KpnI and ApaI restriction sites. 3) Inserted PCR amplified Inv fragment (sense orientation) upstream pAgp promoter into construct B with flanking ApaI and EcoRI restriction sites. 4) Inserted PCR amplified Inv fragment (anti-sense orientation) upstream pGbss promoter into construct C with flanking EcoRI and SacI restriction sites. 5) Inserted T-DNA region of constructs A-C into KpnI-SacI region of pSIM1278 backbone.

Silencing was achieved by introducing inverted repeats containing sequences derived from the genes and promoters targeted for silencing. Although there are a number of parallel pathways involved in double-stranded RNA mediated silencing, transcription of these inverted repeats is thought to be processed by the cellular machinery involved in the viral defense (Fusaro et al. 2006). X17 potatoes contain three unique cassettes, which contain sequence from a total of five different potato genes. The pSIM1278 construct consists of two gene silencing cassettes (see FIG. 4, upper construct). One cassette contains an inverted repeat of sequence from two genes, asparagine synthetase-1 (Asn1) and polyphenol oxidase-5 (Ppo5). The second cassette includes sequence from the promoters of the starch associated genes, R1 (531-bp) and phosphorylase-L (PhL) (508-bp). The final cassette was introduced through the pSIM1678 construct, which includes an inverted repeat containing sequence from the vacuolar invertase (VInv) gene (see FIG. 4, lower construct).

All three silencing cassettes are regulated by the same set of well-characterized and tissue-specific promoters from the Agp and Gbss genes of potato, which are highly active in tubers compared with photosynthetically-active tissues and roots (Nakata et al. 1994; Visser et al. 1991). Therefore, expression and gene silencing was expected to be most effective in and largely limited to tubers.

The expression of all five target genes was characterized by northern blot analysis to determine the effectiveness of gene silencing from each cassette. And, as shown by Table 5 below, all five genes were shown to be down-regulated in tubers.

TABLE 5

Summary of RNAi-Target Gene Expression in X17 Tissues

| Gene | Tuber | Leaf | Stem | Root | Flower |
|---|---|---|---|---|---|
| Asn1 | ✓[1] | ✓ | — | — | ✓ |
| Ppo5 | ✓ | — | — | — | — |
| PhL | ✓ | — | — | — | — |
| R1 | ✓ | — | — | — | — |
| VInv | ✓ | — | — | — | ✓ |

[1] ✓ = down-regulated,
— = not down-regulated,
n/o = not observed.

Tuber-specific down-regulation of all targeted genes was observed in the X17 event. Expression levels in other tissues were unaffected, except for small reductions of Asn1 in leaf and Asn1 and VInv in flowers Example 9

Potato Cultivar X17 Characterization Summary

Potato variety X17 addresses the need of the potato industry to improve quality by increasing resistance to late blight, reducing expression of the enzyme responsible for black spot bruise and to reduce acrylamide through lowering the concentration of the reactants, namely asparagine and reducing sugars. Potato variety X17 was transformed with nucleic acid sequences that are native to the potato plant genome and does not contain foreign DNA, Agrobacterium DNA, viral markers or vector backbone sequences In addition, agronomic studies were conducted to ensure that the events grew the same as conventional controls, with the exception of the characteristics associated with the trait.

Field trials were conducted at ten U.S. sites during 2013 and 2014. The purpose of this study was to evaluate the phenotypic performance, tubers, and ecological interactions of X17 potatoes compared with a Ranger Russet control.

The phenotypic, tuber, and ecological interaction data collected did not indicate any meaningful differences between X17 and the Ranger Russet control.

There were no statistically significant differences detected for any of the phenotypic characteristics, indicating that X17 is comparable to Ranger Russet in terms of phenotype.

Results of the tuber assessment indicated that specific gravity, high sugar, and fry color were different, but within the range of values seen in conventional potatoes.

These differences demonstrate an improvement in the tuber quality of X17.

The lack of differences for insect, disease, and abiotic stressors, as well as arthropod abundance, supports a conclusion that the ecological interactions of X17 are the same as conventional potatoes.

TABLE 6

Phenotypic, Yield, and Grading Characteristics

| Characteristic | Variety | N | Mean | P-Value | SD | CVR Min | CVR Max |
|---|---|---|---|---|---|---|---|
| Phenotypic Performance | | | | | | | |
| Early Emergence (%) | X17 | 40 | 50.6 | 0.1754 | 23.5 | 0.0 | 100.0 |
|  | Ranger Ctrl | 40 | 61.7 |  | 21.4 |  |  |
| Final Emergence (%) | X17 | 40 | 89.7 | 0.4499 | 11.2 | 10.6 | 100.0 |
|  | Ranger Ctrl | 40 | 94.2 |  | 7.5 |  |  |
| Stems Per Plant (#) | X17 | 40 | 2.6 | 0.6239 | 1.4 | 1.0 | 6.0 |
|  | Ranger Ctrl | 40 | 2.5 |  | 1.5 |  |  |
| Plant Vigor (1-5 Scale) | X17 | 40 | 3.5 | 0.9550 | 0.9 | 1.3 | 5.0 |
|  | Ranger Ctrl | 40 | 3.5 |  | 1.0 |  |  |
| Plant Height (cm) | X17 | 40 | 57.9 | 0.8712 | 16.0 | 16.4 | 108.7 |
|  | Ranger Ctrl | 40 | 58.5 |  | 16.6 |  |  |
| Vine Desiccation (%) | X17 | 40 | 21.1 | 0.5728 | 20.3 | 0.0 | 100.0 |
|  | Ranger Ctrl | 40 | 24.9 |  | 21.1 |  |  |
| Tuber Evaluation | | | | | | | |
| Total Yield (cwt/a) | X17 | 40 | 562.7 | 0.9484 | 207.8 | 89.2 | 1410.6 |
|  | Ranger Ctrl | 40 | 564.3 |  | 221.8 |  |  |
| US#2 Yield (cwt/a) | X17 | 40 | 452.8 | 0.4995 | 174.6 | 118.9 | 693.5 |
|  | Ranger Ctrl | 40 | 477.4 |  | 178.2 |  |  |
| Tubers Per Plant (#) | X17 | 40 | 7.1 | 0.3805 | 2.1 | 3.1 | 19.5 |
|  | Ranger Ctrl | 40 | 6.2 |  | 1.9 |  |  |
| Tubers 4-6 oz (%) | X17 | 40 | 19.5 | 0.2254 | 7.6 | 4.6 | 41.1 |
|  | Ranger Ctrl | 40 | 16.7 |  | 7.1 |  |  |
| Tubers 6-10 oz (%) | X17 | 40 | 25.4 | 0.2607 | 9.2 | 14.0 | 41.2 |
|  | Ranger Ctrl | 40 | 28.6 |  | 9.2 |  |  |
| Tubers 10-14 oz (%) | X17 | 40 | 14.1 | 0.1052 | 9.7 | 1.0 | 33.2 |
|  | Ranger Ctrl | 40 | 17.2 |  | 9.8 |  |  |
| Tubers >14 oz (%) | X17 | 40 | 13.6 | 0.7151 | 14.6 | 0.0 | 51.5 |
|  | Ranger Ctrl | 40 | 15.1 |  | 13.4 |  |  |
| Specific Gravity | X17 | 40 | 1.090 | 0.0286 | 0.008 | 0.835 | 1.171 |
|  | Ranger Ctrl | 40 | 1.086 |  | 0.011 |  |  |
| High Sugar (%) | X17 | 19 | 0.0 | 0.0334 | 0.0 | 0.0 | 84.8 |
|  | Ranger Ctrl | 20 | 9.3 |  | 19.5 |  |  |
| Sugar Ends (%) | X17 | 39 | 1.6 | 0.1351 | 2.9 | 0.0 | 52.6 |
|  | Ranger Ctrl | 40 | 7.1 |  | 11.1 |  |  |
| Fry Color 00 (%) | X17 | 20 | 4.5 | 0.0135 | 3.7 | 0.0 | 4.8 |
|  | Ranger Ctrl | 20 | 1.7 |  | 2.1 |  |  |

TABLE 6-continued

Phenotypic, Yield, and Grading Characteristics

| Characteristic | Variety | N | Mean | P-Value | SD | CVR Min | CVR Max |
|---|---|---|---|---|---|---|---|
| Fry Color 0 (%) | X17 | 39 | 56.6 | 0.1966 | 42.7 | 0.0 | 100.0 |
| | Ranger Ctrl | 40 | 47.8 | | 38.5 | | |
| Fry Color 1 (%) | X17 | 39 | 0.0 | 0.1408 | 0.0 | 0.0 | 29.7 |
| | Ranger Ctrl | 40 | 3.4 | | 8.8 | | |
| Fry Color 2 (%) | X17 | 39 | 0.1 | 0.3416 | 0.8 | 0.0 | 28.8 |
| | Ranger Ctrl | 40 | 3.4 | | 8.5 | | |
| Fry Color 3 (%) | X17 | 39 | 0.0 | 0.1498 | 0.0 | 0.0 | 23.1 |
| | Ranger Ctrl | 40 | 1.2 | | 3.9 | | |
| Fry Color 4 (%) | X17 | 39 | 0.0 | 0.1348 | 0.0 | 0.0 | 79.7 |
| | Ranger Ctrl | 40 | 3.4 | | 13.1 | | |
| Total Internal Defects (%) | X17 | 40 | 0.8 | 0.9104 | 1.9 | 0.0 | 93.8 |
| | Ranger Ctrl | 40 | 1.0 | | 2.1 | | |

Results of the phenotypic performance, tuber evaluation, and ecological interaction studies indicate no meaningful differences between X17 and the Ranger Russet control. There were no differences detected for any of the phenotypic characteristics. For the tuber assessment, specific gravity, high sugar, and fry color were different but within the range of values seen in conventional potatoes. These characteristics are not associated with environmental risk and confirm that X17 quality falls within the range of conventional potatoes. These differences demonstrate an improvement in the tuber quality of X17. The lack of differences for insect, disease, and abiotic stressors as well as arthropod abundance supports a conclusion that the ecological interactions of X17 are not different from conventional potatoes.

Example 10A

Potato Cultivar X17 Late Blight Efficacy 2013 Experiments

The purpose of this study was to evaluate the field efficacy of potato event X17 against foliar late blight (*Phytophthora infestans*).

Field trials were conducted at three sites during 2013. Plots were inoculated with the US-8, US-22, and/or US-23 strains of late blight. The degree of foliar infection was rated throughout the season.

A significant reduction in late blight foliar infection was observed in X17 compared to their non-transformed parental controls, demonstrating efficacy of the late blight resistance trait against the strains of *P. infestans* tested.

Example 10B

Potato Cultivar X17 Late Blight Efficacy 2014 Experiments

The purpose of this study was to evaluate the field efficacy of potato event X17 against foliar late blight (*Phytophthora infestans*).

Field trials were conducted at two sites during 2014. Plots were inoculated with the US-23 strain of late blight. The degree of foliar infection was rated throughout the season.

A significant reduction in late blight foliar infection was observed in X17 compared to their non-transformed parental controls, demonstrating efficacy of the late blight resistance trait against the strain of *P. infestans* tested.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents

REFERENCES

Chawla, R., Shakya, R., and Rommens, C. M. (2012). Tuber-Specific Silencing of Asparagine synthetase-1 Reduces the Acrylamide-Forming Potential of Potatoes Grown in the Field without Affecting Tuber Shape and Yield. Plant Biotechnology Journal 10, 913-924.

Courvalin, P., Weisblum, B., and Davies, J. (1977). Aminoglycoside-Modifying Enzyme of an Antibiotic-Producing Bacterium Acts as a Determinant of Antibiotic Resistance in *Escherichia coli*. Proceedings of the National Academy of Sciences 74, 999-1003.

Garbarino, J. E., and Belknap, W. R. (1994). Isolation of a Ubiquitin-Ribosomal Protein Gene (ubi3) from Potato and Expression of Its Promoter in Transgenic Plants. Plant Molecular Biology 24, 119-127.

Garbarino, J. E., Oosumi, T., and Belknap, W. R. (1995). Isolation of a Polyubiquitin Promoter and Its Expression in Transgenic Potato Plants. Plant Physiology 109, 1371-1378.

Simpson, J., Timko, M. P., Cashmore, A. R., Schell, J., Van Montagu, M., and Herrera-Estrella, L. (1985). Light-Inducible and Tissue-Specific Expression of a Chimaeric Gene under Control of the 5'-Flanking Sequence of a Pea Chlorophyll A/b-Binding Protein Gene. The EMBO Journal 4, 2723-2729.

Smigocki, A. C., and Owens, L. D. (1988). Cytokinin Gene Fused with a Strong Promoter Enhances Shoot Organogenesis and Zeatin Levels in Transformed Plant Cells. Proceedings of the National Academy of Sciences 85, 5131-5135.

VanHaaren, M. J. J., Sedee, N. J. A., de Boer, H. A., Schilperoort, R. A., and Hooykaas, P. J. J. (1989). Mutational Analysis of the Conserved Domains of a T-Region Border Repeat of *Agrobacterium tumefaciens*. Plant Molecular Biology/3, 523-531.

Deposit Information

A tuber deposit of the J. R. Simplot Company proprietary POTATO CULTIVAR X17 disclosed above and recited in the appended claims has been made with the American Type Culture Collection (ATCC), 10801 University Boulevard, Manassas, Va. 20110. The date of deposit was Jun. 17, 2015. The deposit of 50 vials of microtubers was taken from the same deposit maintained by J.R. Simplot Company since prior to the filing date of this application. All restrictions will be irrevocably removed upon granting of a patent, and the deposit is intended to meet all of the requirements of 37 C.F.R. §§1.801-1.809. The ATCC Accession Number is PTA-122248. The deposit will be maintained in the depository for a period of thirty years, or five years after the last request, or for the enforceable life of the patent, whichever is longer, and will be replaced as necessary during that period.

What is claimed is:

1. A potato tuber, or a part of a tuber, of potato cultivar X17, wherein a representative sample of said tuber was deposited under ATCC Accession No. PTA-122248.

2. A potato plant, or a part thereof, produced by growing the tuber, or a part of the tuber, of claim 1.

3. A potato plant having all of the physiological and morphological characteristics of the plant of claim 2, and comprising the insert region of pSIM1278 that is present in cultivar X17 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in X17 which contains the potato late blight resistance gene Rpi-vnt1 and inverted repeats of potato DNA effective for inhibition of expression of the endogenous vacuolar invertase gene VInv.

4. A tissue culture of cells produced from the plant of claim 2, wherein said cells of the tissue culture are produced from a plant part selected from the group consisting of leaf, pollen, embryo, cotyledon, hypocotyl, meristematic cell, root, root tip, pistil, anther, flowers, stem and tuber, and wherein said tissue cultured cells comprise the insert region of pSIM1278 that is present in cultivar X17 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in X17 which contains the potato late blight resistance gene Rpi-vnt1 and inverted repeats of potato DNA effective for inhibition of expression of the endogenous vacuolar invertase gene VInv.

5. A potato plant regenerated from the tissue culture of claim 4, wherein said plant has all of the physiological and morphological characteristics of potato cultivar X17.

6. A potato seed produced by growing the potato tuber, or a part of the tuber, of claim 1, wherein said seed comprises the insert region of pSIM1278 that is present in cultivar X17 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in X17 which contains the potato late blight resistance gene Rpi-vnt1 and inverted repeats of potato DNA effective for inhibition of expression of the endogenous vacuolar invertase gene VInv.

7. A potato plant, or a part thereof, produced by growing the seed of claim 6.

8. A potato plant regenerated from tissue culture of the potato plant of claim 7, wherein said regenerated plant comprises the insert region of pSIM1278 that is present in cultivar X17 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in X17 which contains the potato late blight resistance gene Rpi-vnt1 and inverted repeats of potato DNA effective for inhibition of expression of the endogenous vacuolar invertase gene VInv.

9. A method for producing a potato seed, said method comprising crossing two potato plants and harvesting the resultant potato seed, wherein at least one potato plant is the potato plant of claim 2.

10. A method for producing a potato seed, said method comprising crossing two potato plants and harvesting the resultant potato seed, wherein at least one potato plant is the potato plant of claim 7.

11. A potato seed produced by the method of claim 10, wherein said seed comprises the insert region of pSIM1278 that is present in cultivar X17 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in X17 which contains the potato late blight resistance gene Rpi-vnt1 and inverted repeats of potato DNA effective for inhibition of expression of the endogenous vacuolar invertase gene VInv.

12. A potato plant, or a part thereof, produced by growing said potato seed of claim 11.

13. A potato seed produced from the plant of claim 12, wherein said seed comprises the insert region of pSIM1278 that is present in cultivar X17 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in X17 which contains the potato late blight resistance gene Rpi-vnt1 and inverted repeats of potato DNA effective for inhibition of expression of the endogenous vacuolar invertase gene VInv.

14. The method of claim 9, wherein one of said potato plants is potato cultivar X17 and the second potato plant is transgenic.

15. A method of producing a potato seed, said method comprising crossing two potato plants and harvesting the resultant potato seed, wherein one of said potato plants is the potato plant of claim 7 and the second potato plant is transgenic.

16. A potato plant, or a part thereof, produced by growing the seed produced by the method of claim 14, wherein said plant comprises the insert region of pSIM1278 that is present in cultivar X17 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in X17 which contains the potato late blight resistance gene Rpi-vnt1 and inverted repeats of potato DNA effective for inhibition of expression of the endogenous vacuolar invertase gene VInv.

17. A method of introducing a desired trait into potato cultivar X17, wherein the method comprises:
 (a) crossing a X17 plant, wherein a representative sample of tubers was deposited under ATCC Accession No. PTA-122248, with a plant of another potato cultivar that comprises a desired trait to produce progeny plants, wherein the desired trait is selected from the group consisting of male sterility, herbicide resistance, insect resistance, modified fatty acid metabolism, modified carbohydrate metabolism and resistance to bacterial disease, fungal disease or viral disease;
 (b) selecting one or more progeny plants that have the desired trait;
 (c) backcrossing the selected progeny plants with X17 plants to produce backcross progeny plants;
 (d) selecting for backcross progeny plants that have the desired trait; and
 (e) repeating steps (c) and (d) two or more times in succession to produce selected third or higher backcross progeny plants that comprise the desired trait.

18. A potato plant produced by the method of claim 17, wherein the plant has the desired trait and comprises the insert region of pSIM1278 that is present in cultivar X17 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in X17 which contains the potato late blight resistance gene Rpi-vnt1 and inverted repeats of potato DNA effective for inhibition of expression of the endogenous vacuolar invertase gene VInv.

19. The potato plant of claim 18, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

20. The potato plant of claim 18, wherein the desired trait is insect resistance and the insect resistance is conferred by a transgene encoding a *Bacillus thuringiensis* endotoxin.

21. The potato plant of claim 18, wherein the desired trait is modified fatty acid metabolism or modified carbohydrate metabolism and said desired trait is conferred by a nucleic acid encoding a protein selected from the group consisting of fructosyltransferase, levansucrase, α-amylase, invertase and starch branching enzyme or DNA encoding an antisense of stearyl-ACP desaturase.

22. A method of producing a commodity plant product, comprising obtaining the plant of claim 2, or a part thereof, and producing the commodity plant product from said plant or plant part thereof, wherein said commodity plant product is selected from the group consisting of: fresh whole potatoes, French fries, potato chips, dehydrated potato material, potato flakes and potato granules.

23. The commodity plant product produced by the method of claim 22, wherein said product comprises the insert region of pSIM1278 that is present in cultivar X17 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in X17 which contains the potato late blight resistance gene Rpi-vnt1 and inverted repeats of potato DNA effective for inhibition of expression of the endogenous vacuolar invertase gene VInv.

24. A food product made from the potato tuber of claim 1.

25. A food product made from the potato tuber of claim 1, wherein the food product is a sliced potato tuber food product.

26. A food product made from the potato tuber of claim 1, wherein the food product is a French fry or chip.

27. A heat-processed tuber product obtained from the potato tuber of claim 1.

28. A heat-processed tuber product obtained from the potato tuber of claim 1, wherein the heat processed tuber product is selected from the group consisting of: a French fry, a chip, and a baked potato.

29. A heat-processed tuber product obtained from the potato tuber of claim 1, wherein the heat processed tuber product is selected from the group consisting of: a French fry, a chip, and a baked potato, wherein the heat-processed tuber product has a concentration of acrylamide that is at least 50% lower, 60% lower, 70% lower, 80% lower, 85% lower, or more, than the concentration of acrylamide of a control heat-processed tuber product that is obtained from a control potato plant that does not comprise the insert region of pSIM1278 and pSIM1678 that is present in cultivar X17.

* * * * *